(12) United States Patent
Baker et al.

(10) Patent No.: US 7,626,079 B2
(45) Date of Patent: Dec. 1, 2009

(54) REGULATION OF PEROXISOMAL FATTY ACID TRANSPORT IN PLANTS

(75) Inventors: Alison Baker, Leeds (GB); Stephen Slocombe, Leeds (GB); Ian Graham, York (GB)

(73) Assignee: The University of Leeds, Leeds (GB)

( * ) Notice: Subject to any disclaimer, the term of this patent is extended or adjusted under 35 U.S.C. 154(b) by 111 days.

(21) Appl. No.: 10/486,376

(22) PCT Filed: Jul. 19, 2002

(86) PCT No.: PCT/GB02/03334

§ 371 (c)(1),
(2), (4) Date: Jul. 16, 2004

(87) PCT Pub. No.: WO03/008597

PCT Pub. Date: Jan. 30, 2003

(65) Prior Publication Data

US 2004/0244078 A1 Dec. 2, 2004

(30) Foreign Application Priority Data

Jul. 20, 2001 (GB) ................................. 0117727.8
Apr. 5, 2002 (GB) ................................. 0207883.0

(51) Int. Cl.
*C12N 15/82* (2006.01)
*A01H 5/00* (2006.01)
*C07H 21/04* (2006.01)

(52) U.S. Cl. ...................... 800/281; 800/285; 800/286; 800/295; 800/298; 435/419; 435/468; 435/320.1; 536/23.2; 536/23.6

(58) Field of Classification Search ....................... None
See application file for complete search history.

(56) References Cited

U.S. PATENT DOCUMENTS 5,702,933 A * 12/1997 Klee et al. ................... 800/283
2005/0164192 A1* 7/2005 Graham et al. ................. 435/6

OTHER PUBLICATIONS

Davies et al. The *Arabidopsis thaliana* ATP-binding cassette proteins: an emerging superfamily. (2000) Plant, Cell and Environment, vol. 23, pp. 431-443.*
Lewin, B. (1994) Genes V, Oxford University Press, Oxford, New York, Tokyo, p. 1254.*
Taylor C. B. Factories of the Future? Metabolic Engineering in Plant Cells. (1998) The Plant Cell, vol. 10, pp. 641-644.*
Butler et al. A perspective of metabolic engineering strategies: moving up the systems hierarchy. (2003) Biotech. and Bioeng., vol. 84, pp. 815-821.*
Elomaa et al. Transformation of antisense constructs of the chalcone synthase gene superfamily into *Gerbera hybrida*: differential effect on the expression of family members. (1996) Molecular Breeding, vol. 2, pp. 41-50.*
Bevan et al. Hypothetical protein T5J17.20—*Arabidopsis thaliana* (1999) Accession T06091, pp. 1-2.*
Colliver et al. Differential modification of flavonoid and isoflavonoid biosynthesis with an antisense chalcone synthase construct in transgenic *Lotus corniculatus*. (1997) PMB, vol. 35, pp. 509-522.*
Lazar et al. Transforming growth factor alpha: mutation of aspartic acid 47 and leucine 48 results in different biological activities. (1988) MCB, vol. 8, pp. 1247-1252.*
Hill et al. Functional analysis of conserved histidines in ADP-Glucose pyrophosphorylase from *Escherichia coli*. (1998) Biochem. and Biophys. Res. Comm., vol. 244, pp. 573-577.*
Guo et al. Protein tolerance to random amino acid change. (2004) PNAS, vol. 101, pp. 9205-9210.*
GenBank Accession AL035708 (1999), pp. 1-50.*
Asamizu et al. AV523713 *Arabidopsis thaliana* aboveground organs two to six-week old *Arabidopsis thaliana* cDNA clone APZL37d10F 3', mRNA sequence. (2000) GenBank Accession AV523713; pp. 1-2.*
GenBank AV523713 Revision History; p. 1 of 1.*
Volckaert et al. *Arabidopsis thaliana* DNA chromosome 4, contig fragment No. 92. (2000) GenBank Accession AL161596; pp. 1-55).*
"*Arabidopsis thaliana* Peroxisomal ABC Transporter PXA1 mRNA, Complete cds" Accession No. AF387120, EBI Database, Nov. 22, 2001.
"*Arabidopsis thaliania* DNA Chromosome 4, BAC Clone T5J17" Accession No. AL035708, EBI Database, Sep. 21, 1999.
"Hypothetical 154.8 kDa Protein" Accession No. Q9SMR8, EBI Database, Feb. 1, 2003.
"Peroxisomal ABC Transporter PXA1 (ABC Transporter)" Accession No. Q94FB9, EBI Database, Feb. 1, 2003.
"Peroxisomal ABC Transporter" Accession No. Q8VWH7, EBI Database, Feb. 1, 2003.
Zolman et al. "The *Arabidopsis* PXA1 Mutant is Defective in an ATP-Binding Cassette Transporter-Like Protein Required for Peroxisomal Fatty Acid β-Oxidation" *Plant Physiology* 127:1266-1278 (2001).
Davies and Coleman "The *Arabidopsis thaliana* ATP-Binding Cassette Proteins: An Emerging Superfamily" *Plant, Cell and Environment* 23:431-443 (2000).
Footitt et al. "Control of Germination and Lipid Mobilization by COMATOSE, the *Arabidopsis* Homologue of Human ALDP" *The EMBO Journal* 21(12):2912-2922 (2002).
Gaedke et al. "The *Arabidopsis thaliana* ABC Transporter *At*MRP5 Controls Root Development and Stomata Movement" *The EMBO Journal* 20(8):1875-1887 (2001).
Hayashi et al. "Ped3p is a Peroxisomal ATP-Binding Cassette Transporter that might Supply Substrates for Fatty Acid β-Oxidation" *Plant Cell Physiol*. 43(1):1-11 (2002).

(Continued)

*Primary Examiner*—Cathy Kingdon Worley
(74) *Attorney, Agent, or Firm*—Myers Bigel Sibley & Sajovec, P.A.

(57) ABSTRACT

A nucleic acid which encodes a peroxisomal fatty acid transporter, uses thereof and a method of genetic manipulation of peroxisomal fatty acid transport and/or Metabolism. The nucleic acid and its products are especially for use in regulation of peroxisomal fatty acid transport in plant and in controlling the spectrum of fatty acids which can be utilised by the plant.

32 Claims, 9 Drawing Sheets

OTHER PUBLICATIONS

Hettema and Tabak "Transport of Fatty Acids and Metabolites Across the Peroxisomal Membrane" *Biochimica et Biophysica Acta* 1486:18-27 (2000).

International Search Report corresponding to PCT/GB02/03334; mailed Mar. 12, 2003.

Russell et al. "The *Arabidopsis* COMATOSE Locus Regulates Germination Potential" *Development* 127:3759-3767 (2000).

Tugal et al. "*Arabidopsis* 22-Kilodalton Peroxisomal Membrane Protein. Nucleotide Sequence Analysis and Biochemical Characterization" *Plant Physiology* 120:309-320 (1999).

Germain et al. "Requirement for 3-ketoacyl-CoA thiolase-2 in peroxisome development, fatty acid β-oxidation and breakdown of triacylglycerol in lipid bodies of *Arabidopsis* seedlings" *The Plant Journal* 28(1):1-12 (2001).

Hayashi et al. "2,4-Dichlorophenoxybutyric Acid-Resistant Mutants of Arabidopsis Have Defects in Glyoxysomal Fatty Acid β-Oxidation" *The Plant Cell* 10:183-195 (1998).

Hettema et al. "The ABC transporter proteins Pat1 and Pat2 are required for import of long-chain fatty acids into peroxisomes of *Saccharomyces cerevisiae*" *The EMBO Journal* 15(15): 3813-3822 (1996).

Hooks et al. "Long-chain acyl-CoA oxidases of *Arabidopsis*" *The Plant Journal* 20(1):1-13 (1999).

Larson et al. "A novel technique for the sensitive quantification of acyl CoA esters from plant tissues" *The Plant Journal* 25(1):115-125 (2001).

Mannaerts et al. "Evidence that peroxisomal acyl-CoA synthetase is located at the cytoplasmic side of the peroxisomal membrane" *Biochem. J.* 204:17-23 (1982).

Mosser et al. "Putative X-linked adrenoleukodystrophy gene shares unexpected homology with ABC transporters" *Nature* 361:726-730 (1993).

Olsen et al. "ACYL-CoA Synthetase Activity Associated with Rapeseed Lipid Body Membranes" *Phytochemistry* 36(1):7-9 (1994).

Zolman et al. "Genetic Analysis of Indole-3-butyric Acid Responses in *Arabidopsis thaliana* Reveals Four Mutant Classes" *Genetics* 156:1323-1337 (2000).

Ogras et al. "Reduction of Lignin in Tobacco Through the Expression of an Antisense Caffeic Acid *O*-methyltransferase" *Turk J Bot* 24:221-226 (2000).

Salehuzzaman et al. "Isolation and Characterization of a cDNA Encoding Granule-Bound Starch Synthase in Cassava (*Mainhot esculenta* Crantz) and its Antisense Expression in Potato" *Plant Molecular Biology* 23:947-962 (1993).

Temple et al. "Modulation of Glutamine Synthetase Gene Expression in Tobacco by the Introduction of an Alfalfa Glutamine Synthetase Gene in Sense and Antisense Orientation: Molecular and Biochemical Analysis" *Mol Gen Genet* 236:315-325 (1993).

Van Der Krol et al. "An Anti-sense Chalcone Synthase Gene in Transgenic Plants Inhibits Flower Pigmentation" *Nature* 333:866-869 (1988).

Weiting et al. "Reduced Lignin in Transgenic Plants Containing a Caffeic Acid *O*-methyltransferase Antisense Gene" *Transgenic Research* 3:120-126 (1994).

\* cited by examiner

```
HSALD   437  PRELE        AGSGTIGRSGVRVEGPLKI
HSPMP70 407  ERTMVS       ----KGIEGVQVIPLIPGA
ATCTSA  430  KSSFOR  RS-------------------RNY
ATCTSB  330  SGVTS        -----------------------TSR
SCPXA1  429  SILSIRT      ASRNSNLLPTTDNSQDAI
SCCTS   452  GDDEK  PR    -------------E--
                                                        Walker A
                                                       ----------

HSALD   487  --------------------------E
HSPMP70 453  --------------------------DV
ATCTSA  461  --------------------------N
ATCTSB  360  --------------------------K
SCPXA1  489  KLTFQIPLHIDPITSKSNSIQDLSKANDIK
SCCTS   485  ----------------------------

HSALD   523  L      SV Y     ----------PP
HSPMP70 489  L             ----------ERR
ATCTSA  497  L             GVGS-----DLNKE
ATCTSB  396             VC          SLDIKEL----GSG
SCPXA1  549             NKNGLLSIP--------SE
SCCTS   521             TPNKNEQSKLIMPRRTVDRDCA

HSALD   565  ---------   MQR
HSPMP70 531  ---------   QKR
ATCTSA  543  ---------GQESEL
ATCTSB  451  AAKLYTSGESSTEAGS
SCPXA1  594  ---------    FFD
SCCTS   581  ---------YHNDYD
                                 C sequence     Walker B
                                 ----------    ----------

HSALD   595  ---------     CD
HSPMP70 561  ---------     QD
ATCTSA  572  ---------P  KEVN
ATCTSB  492  ---------   PTTN
SCPXA1  627  ---------    P AD
SCCTS   631  QSPCAIKVRDA   S   RN

HSALD   644
HSPMP70 610
ATCTSA  621  AAKV
ATCTSB  541     V
SCPXA1  676      NLL
SCCTS   691       N   ONF

HSALD   702  QLAG-------------------IPKM   RR  QELCQ    GEAVAPAHVPAPSPQGP
HSPMP70
ATCTSA  679  SDTDRQNDAMVVQRAFAAARK SATNSKAQSY  TQ  IARSP  DKSVVLPRFPQPQTSQR
ATCTSB
SCPXA1  736  RKLERVKG--------------------WEDERTK REKLE
SCCTS   749  ILDQQVPLWERKLKDLTIAKESNIIRKSETNL LFEKIEDPKTSKSNALFNANKGQRITS

HSALD   738  GGLQGAST-------------------------------------
HSPMP70
ATCTSA  739  ALPSRVAAMLNV----------------------------------
ATCTSB
SCPXA1
SCCTS   809  PTGQETSKRLPLFSQPSSSASSNLLRNNKSLNKKVKTRKEEGKE
```

Abbrevations: M, marker; dpi, days post imbibition.

Figure 3 Expression and purification of 2nd ATPase domain of CTS2p

Sc- cell sample. P-pellet fraction. Sn-supernatant fraction. Sm solubilised sample loaded on NTA agarose. FT- flow through. W1,2 wash fractions. E1-5 elution fractions.

Figure 5. Location of T-DNA insertions in three CTS knockouts R6, F27 and F12. Exons are shown as dark shaded boxes. Non coding transcribed regions are indicated by light shading.

A
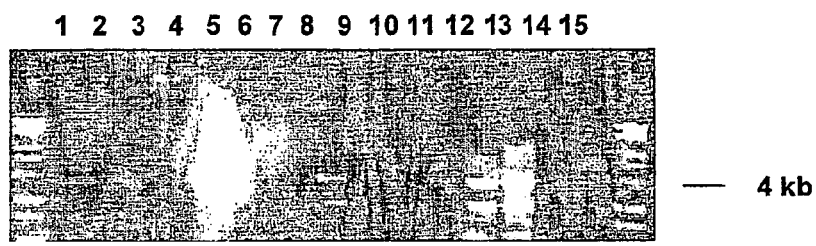
B
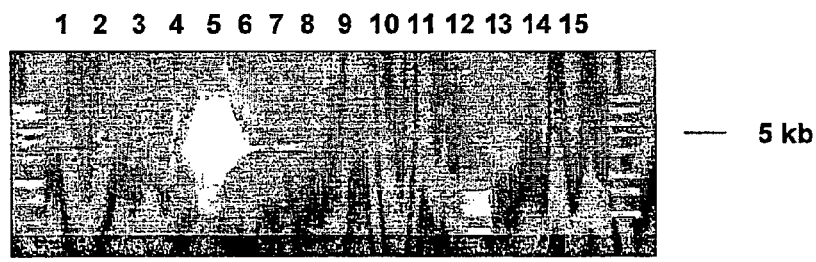
C 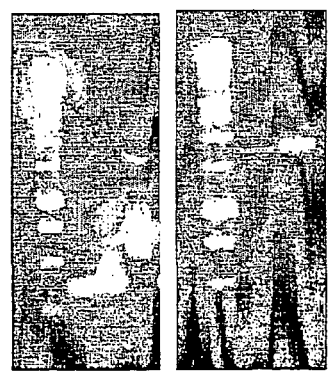
D
Figure 6.

Figure 7. CTS is localised to peroxisomes. Sucrose density gradient showing the localisation of peroxisomal markers catalase (closed circles) and 3-ketoacyl thiolase (KAT), ER marker calreticulin (CAL), mitochondrial marker adenine nucleotide translocator (ANT) and chlorophyll (open circles). PXA2 antigen follows the distribution of catalase and thiolase.

REGULATION OF PEROXISOMAL FATTY ACID TRANSPORT IN PLANTS

CROSS-REFERENCE TO RELATED APPLICATIONS

The present application is a 35 U.S.C. § 371 National Phase Application of International Application Serial No. PCT/GB02/03334, filed Jul. 19, 2002 and published in English as PCT Publication No. WO 03/008597 A2 on Jan. 30, 2003, which claims priority to Great Britain Patent Application Serial No. 0207883.0, filed Apr. 5, 2002 and Great Britain Patent Application Serial No. 0117727.8, filed Jul. 20, 2001, the disclosures of each of which are incorporated herein by reference in their entireties.

The present invention relates to an isolated nucleic acid, uses thereof and a method of genetic manipulation of peroxisomal fatty acid transport and/or metabolism, means therefor and products thereof especially for use in regulation of plant growth and in controlling the spectrum of fatty acids which can be utilised by the plant.

BACKGROUND TO THE INVENTION

Fatty acids are major carbon and energy stores in the seeds of many agriculturally important species. For the plant they are essential reserves that support germination and seedling establishment until the plant can manufacture its own building blocks and energy through photosynthesis. Recent published data shows that blocking the mobilisation of these fatty acids prevents or severely compromises establishment (Hayashi et al., 1998, Germain et al., 2001). Clearly, efficient germination and seedling establishment are of vital importance to farmers. In addition, the fatty acids deposited in seeds renders them important foodstuffs for humans and animals. There is considerable interest in modifying the levels and composition of fatty acids in seeds to improve their nutritional quality and health benefit. Furthermore, there is considerable interest in engineering crop plants to produce novel fatty acids with industrial benefit. These can be used as feedstocks for the chemical and healthcare industries, with the aim of reducing reliance on petrochemical feedstocks, it is therefore desirable to produce these molecules in a more ecologically friendly and sustainable way and to develop non-food crops for European agriculture.

Plants that are engineered to produce altered fatty acids rarely produce economically viable levels in seeds. The reasons for this are probably complex but one factor may be their turnover, i.e. some proportion is broken down as they are made. Furthermore, if high levels can be achieved this may compromise the ability of these plants to germinate and establish if these altered fatty acids cannot be used efficiently. Clearly this is detrimental to the commercialisation of these plants.

Fatty acids in seeds are stored in oil bodies in the form of triacylglycerols (3 fatty acid molecules joined to a glycerol backbone) which are laid down during seed development. During germination free fatty acids are released by the action of lipases and the fatty acids enter the β-oxidation pathway which is housed within a specialised organelle the glyoxysome. The fatty acids are then metabolised to produce energy and building blocks for the cell. Control of biochemical pathways frequently resides near the beginning of the pathway and in several cases transport steps have been shown to exert high flux control coefficients. This means that transporting a molecule, for example, from compartment A to compartment B is often an important step in determining the overall rate of the pathway.

There is some evidence to suggest from human studies that proteins of the ATP Binding Cassette family (referred to as ABCs) are involved in fatty acid transport. ABCs are integral membrane proteins that transport a wide variety of molecules across membranes. It is known from the prior art that X-linked adrenoleukodystrophy (X-ALD) is associated with a particular gene mutation (Moser et al., 1993). The clinical symptoms of the disease, results in increasing neurological impairment, progressive mental and physical disability, and eventually death in late childhood or early teens. Biochemically these patients fail to break down very long chain fatty acids. The gene mutated in X-ALD is an ABC transporter closely related to but not identical to another mammalian peroxisomal ABC transporter, PMP70. It is now known that there are 4 of these peroxisomal ABC genes in humans (PMP70, PMP70R, ALD and ALDR. In addition, two homologous genes have been identified in yeast *S. cerevisiae* (PXA1 and PXA2 also known as PAT1 and PAT2) and have been shown to be transporters of fatty acyl CoAs (Hettema et al., 1996). PXA2 is also known as the COMATOSE (CTS) gene (Russell et al., 2000; Footitt et al., 2002).

Glyoxysomes are cytoplasmic organelles unique to plants. Glyoxysomes are a specialised form of peroxisomes but they also contain enzymes of the glyoxalate cycle. They are abundantly present in the endosperm or cotyledons of oil-rich seeds. It is not known how fatty acids are transported into glyoxysomes.

It is therefore desirous to identify a transport protein or a regulator protein that is involved with the rate of entry of fatty acids into the degradation pathway. Identification and characterisation of the proteins that transport fatty acids into glyoxysomes would offer an attractive target for biotechnology with a view to repress or promote growth or to alter the spectrum of fatty acids which can be utilised by the plant.

STATEMENTS OF THE INVENTION

According to a first aspect of the invention there is provided an isolated nucleic acid comprising a nucleotide sequence which encodes a polypeptide which functions as a fatty acid transporter in plants selected from the group consisting of:
 (i) a nucleic acid sequence depicted in SEQ ID NO: 1,
 (ii) a nucleic acid sequence which is derived from the sequence depicted in SEQ ID NO: 1 according to the degeneracy of the genetic code,
 (iii) derivatives of the sequence depicted in SEQ ID NO: 1, which encodes polypeptides having preferably at least 30% homology to the sequence encoding amino acid sequences depicted in SEQ ID NO: 2 and which sequences function as a fatty acid transporter.

The nucleic acids of the present invention are conveniently referred to as the CTS gene.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers. Accordingly, one aspect of the invention pertains to isolated nucleic acid molecules (e.g., cDNAs) comprising a nucleotide sequence encoding a fatty acid transporter protein or biologically active portions thereof, as well as nucleic acid fragments suitable as primers or hybridization probes for the detection or amplification of fatty acid transporter-encoding nucleic acid (e.g., DNA or mRNA). In particularly preferred embodiments, the isolated nucleic acid molecule comprises one of the nucleotide sequences set forth in Sequence SEQ ID NO: 1 or the coding region or a complement thereof of one of these nucleotide sequences. In other particularly preferred embodiments, the isolated nucleic acid molecule of the invention comprises a nucleotide sequence which hybridizes to or is at least about 50%, preferably at least about 60%, more preferably at least about 70%, 80% or 90%, and even more preferably at least about 95%, 96%, 97%, 98%, 99% or more homologous to a nucleotide sequence as in Sequence SEQ ID NO: 1, or a portion thereof. In other preferred embodiments, the isolated nucleic acid molecule encodes one of the amino acid sequences set forth in Sequence SEQ ID NO: 2. The preferred fatty acid transporter-gene of the present invention also preferably possess at least one of the fatty acid transporter activities described herein. These may include transport of fatty acids and/or acyl CoAs of varying chain lengths, degree of unsaturation and substitution, and their analogues and derivatives and/or other amphipathic molecules such as 2,4 dichlorophenoxybutyric acid and indole butyric acid and their analogues and derivatives.

In another embodiment, the isolated nucleic acid molecule is at least 15 nucleotides in length and hybridizes under stringent conditions to a nucleic acid molecule comprising a nucleotide sequence of SEQ ID NO: 1. Preferably, the isolated nucleic acid molecule corresponds to a naturally-occurring nucleic acid molecule. More preferably, the isolated nucleic acid encodes a naturally-occurring *Arabidopsis thaliana* fatty acid transporter, or a biologically active portion thereof.

Alternatively, the isolated fatty acid transporter can comprise an amino acid sequence which is encoded by a nucleotide sequence which hybridizes, e.g., hybridizes under stringent conditions, or is at least about 50%, preferably at least about 60%, more preferably at least about 70%, 80%, or 90%, and even more preferably at least about 95%, 96%, 97%, 98,%, or 99% or more homologous, to a nucleotide sequence of SEQ ID NO: 1. It is also preferred that the preferred forms of fatty acid transporters also have one or more of the fatty acid transporter activities described herein. Nucleic acid molecules corresponding to natural variants and non-*Arabidopsis thaliana* homologues, derivatives or analogues of the *Arabidopsis thaliana* fatty acid transporter cDNA of the invention can be isolated based on their homology to *Arabidopsis thaliana* fatty acid transporter nucleic acid disclosed herein using the *Arabidopsis thaliana* cDNA, or a portion thereof, as a hybridization probe according to standard hybridization techniques under stringent hybridization conditions. Accordingly, in another embodiment, an isolated nucleic acid molecule of the invention is at least 15 nucleotides in length and hybridizes under stringent conditions to the nucleic acid molecule comprising a nucleotide sequence of SEQ ID NO: 1. In other embodiments, the nucleic acid is at least 25, 50, 100, 250 or more nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in Current Protocols in Molecular Biology, John Wiley & Sons, N.Y. (1989), 6.3.1-6.3.6. A preferred, non-limiting example of stringent hybridization conditions are hybridization in 6× sodium chloride/sodium citrate (=SSC) at about 45° C., followed by one or more washes in 0.2×SSC, 0.1% SDS at 50-65° C. As known by the skilled artisan such hybridization conditions differ depending on the type of the nucleic acid and if for example organic solvents are present in view of the temperature and the concentration of the buffer. The temperature for example differs under "standard hybridization conditions" depending on the type of the nucleic acid between 42° C. and 58 C in aqueous buffer with a concentration of 0.1 to 5×SSC (pH 7.2). In the event that organic solvent is present in the before mentioned buffer for example 50% formamide the temperature under standard conditions is about 42° C. Preferably hybridisation conditions for DNA:DNA-hybrids are for example 0.1×SSC and 20° C. to 45° C., preferably between 30° C. to 45° C. Preferably hybridisation conditions for DNA:RNA-hybrids are for example 0.1×SSC and 30° C. to 55° C., preferably between 45° C. to 55° C. The before mentioned hybridization temperatures are estimated for example for a nucleic acid of about 100 bp (=base pairs) in length with G+C-content of 50% in the absence of formamide. The skilled worker knows how to estimate the necessary hybridization conditions according to textbooks such as the one mentioned above or from the following textbooks Sambrook et al., "Molecular Cloning", Cold Spring Harbor Laboratory, 1989; Hames and Higgins (eds.), 1985, "Nucleic Acids Hybridization: A Practical Approach", IRL Press at Oxford University Press, Oxford; Brown (ed), 1991, "Essential Molecular Biology: A Practical Approach", IRL Press at Oxford University Press, Oxford. This is also true for stringent or low stringent hybridization conditions.

Preferably, an isolated nucleic acid molecule of the invention hybridizes under stringent conditions to a sequence of SEQ ID NO: 1 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural *Arabidopsis thaliana* fatty acid transporter.

In addition to naturally-occurring variants of the fatty acid transporter sequence that may exist in the population, the skilled artisan will further appreciate that changes can be introduced by mutation into a nucleotide sequence of SEQ ID NO: 1, thereby leading to changes in the amino acid sequence of the encoded fatty acid transporter, without altering the functional ability of the fatty acid transporter. For example, nucleotide substitutions leading to amino acid substitutions at "non-essential" amino acid residues can be made in a sequence of SEQ ID NO: 1. A "non-essential" amino acid residue is a residue that can be altered from the wild-type sequence of one of the fatty acid transporters (SEQ ID NO: 2) without altering the activity of said fatty acid transporter, whereas an "essential" amino acid residue is required for fatty acid transporter activity. Other amino acid residues, however, (e.g., those that are not conserved or only semi-conserved in the domain having fatty acid transporter activity) may not be essential for activity and thus are likely to be amenable to alteration without altering fatty acid transporter activity.

In another embodiment, the isolated nucleic acid molecule encodes a protein or portion thereof wherein the protein or portion thereof includes an amino acid sequence which is sufficiently homologous to an amino acid sequence of sequence SEQ ID NO: 2 such that the protein or portion thereof maintains a fatty acid transporter activity. Preferably, the protein or portion thereof encoded by the nucleic acid molecule maintains the ability to participate in the metabolism of compounds necessary for the construction of fatty acids especially PUFAs or cellular membranes of plants or in the transport of molecules across these membranes. In one embodiment, the protein encoded by the nucleic acid molecule is at least about 50%, preferably at least about 60%, and more preferably at least about 70%, 80%, or 90% and most preferably at least about 95%, 96%, 97%, 98%, or 99% or more homologous (=identity) to an amino acid sequence of Sequence SEQ ID NO: 2.

Further, DNAs of which code for proteins of the present invention, or DNAs which hybridize to that of SEQ ID NO:1 but which differ in codon sequence from SEQ ID NO:1 due to the degeneracy of the genetic code, are also part of this invention. The degeneracy of the genetic code, which allows different nucleic acid sequences to code for the same protein or peptide, is well known in the literature. See, e.g., U.S. Pat. No. 4,757,006 to Toole et al. at Col. 2, Table 1.

Sequence identity: the similarity between two nucleic acid sequences, or two amino acid sequences, is expressed in terms of the similarity between the sequences, otherwise referred to as a sequence identity. Sequence identity is frequently measured in terms of percentage identity (or similarity or homology); the higher the percentage, the more similar the two sequences are. Homologues or orthologues of the protein, and the corresponding cDNA or gene sequence, will possess a relatively high degree of sequence identity when aligned using standard methods. This homology will be more significant when the orthologous proteins or genes or cDNAs are derived from species that are more closely related (e.g., human and chimpanzee sequences), compared to species more distantly related (e.g. human and C. elegans sequences).

Methods of alignment of sequences for comparison are well known in the art. Various programs and alignment algorithms are described in: Smith & Waterman *Adv. Appl. Math.* 2: 482, 1981; Needleman & Wunsch *J. Mol. Biol.* 48: 443, 1970; Pearson & Lipman *Proc. Natl. Acad. Sci. USA* 85: 2444, 1988; Higgins & Sharp *Gene,* 73: 237-244, 1988; Higgins & Sharp *CABIOS* 5: 151-153, 1989; Corpet et al. *Nuc. Acids Res.* 16, 10881-90, 1988; Huang et al. *Computer Appls. In the Biosciences* 8, 155-65, 1992; and Pearson et al. *Meth. Mol. Bio.* 24, 307-31, 1994. Altschul et al. (J. Mol. Biol. 215:403-410, 1990), presents a detailed consideration of sequence alignment methods and homology calculations.

The NCBI Basic Local Alignment Search Tool (BLAST) (Altschul et al. *J. Mol. Biol.* 215:403-410, 1990) is available from several sources, including the National Center for Biotechnology Information (NCBI, Bethesda, Md.) and on the Internet, for use in connection with the sequence analysis blastp, blastn, blastx, tblastn and tblastx. By way of example, for comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment may for example be performed using the Blast 2 sequences function, employing the PAM30 matrix set to default parameters (open gap 9, extension gap 1 penalties).

According to a yet further aspect of the invention there is provided a gene construct comprising an isolated nucleic acid having the sequence SEQ ID NO: 1 as herein before described, wherein the nucleic acid is functionally linked to one or more regulatory signals.

Accordingly, another embodiment of the invention is a novel gene construct comprising an isolated nucleic acid derived from a plant which encodes a polypeptide which functions as fatty acid transporter or the gene sequence of SEQ ID No. 1, its homologous, derivatives or analogous as defined above which have been functionally linked to one or more regulatory signals, advantageously to increase gene expression. Examples of these regulatory sequences are sequences to which inducers or repressors bind and thus regulate the expression of the nucleic acid. In addition to these novel regulatory sequences, the natural regulation of these sequences in front of the actual structural genes can still be present and, where appropriate, have been genetically modified so that the natural regulation has been switched off and the expression of the genes has been increased. The gene construct can, however, also have a simpler structure, that is to say no additional regulatory signals have been inserted in front of the sequence SEQ ID No. 1 or its homologs, and the natural promoter with its regulation has not been deleted. Instead, the natural regulatory sequence has been mutated so that regulation no longer takes place, and gene expression is enhanced. The gene construct may additionally advantageously comprise one or more so-called enhancer sequences functionally linked to the promoter and making increased expression of the nucleic acid sequence possible. It is also possible to insert at the 3' end of the DNA sequences additional advantageous sequences, such as further regulatory elements or terminators. The fatty acid transporter genes may be present in one or more copies in the gene construct. It is advantageous for further genes to be present in the gene construct for insertion of further genes into organisms.

Advantageous regulatory sequences for the novel process are present, for example, in promoters such as cos-, tac-, trp-, tet-, trp-tet-, lpp-, lac-, lpp-lac-, lacIq-, T7-, T5-, T3-, gal-, trc-, ara-, SP6-, 1-PR- or 1-PL-promoter and are advantageously used in Gram-negative bacteria. Further advantageous regulatory sequences are present, for example, in the Gram-positive promoters amy and SPO2, in the yeast or fungal promoters ADC1, MFa, AC, P-60, CYC1, GAPDH, TEF, rp28, ADH or in the plant promoters CaMV/35S [Franck et al., Cell 21 (1980) 285-294], PRP1 [Ward et al., Plant. Mol. Biol. 22 (1993)], SSU, OCS, lib4, usp, STLS1, B33, nos or in the ubiquitin or phaseolin promoter. Also advantageous in this connection are inducible promoters such as the promoters described in EP-A-0 388 186 (benzyl sulfonamide inducible), Plant J. 2, 1992: 397-404 (Gatz et al., Tetracyclin inducible), EP-A-0 335 528 (abscisic acid inducible) or WO 93/21334 (ethanol or cyclohexenol inducible). Additional useful plant promoters are the cytosolic FBPase promoter or ST-LSI promoter of the potato (Stockhaus et al., EMBO J. 8, 1989, 2445), the phosphorybosyl pyrophoshate amido transferase promoter of *Glycine max* (gene bank accession No. U87999) or the noden specific promoter described in EP-A-0 249 676. Particularly advantageous promoters are promoters which allow the expression in tissues which are involved in the fatty acid biosynthesis. Most particularly advantageous are seed specific promoters such as usp-, LEB4-, phaseolin or napin promoter. Additional particularly advantageous promoters are seed specific promoters which can be used for monokotyledones or dikotyledones are described in U.S. Pat. No. 5,608,152 (napin promoter from rapeseed), WO 98/45461 (phaseolin promoter from *Arobidopsis*), U.S. Pat. No. 5,504,200 (phaseolin promoter from *Phaseolus vulgaris*), WO 91/13980 (Bce4 promoter from *Brassica*), Baeumlein et al., Plant J., 2, 2, 1992: 233-239 (LEB4 promoter from leguminosa) said promoters are useful in dikotyledones. The following promoters are useful for example in monokotyledones lpt-2- or lpt-1-promoter from barley (WO 95/15389 and WO 95/23230), hordein promoter from barley and other useful promoters described in WO 99/16890.

It is possible in principle to use all natural promoters with their regulatory sequences like those mentioned above for the novel process. It is also possible and advantageous in addition to use synthetic promoters.

The gene construct may, as described above, also comprise further genes which are to be inserted into the organisms. It is possible and advantageous to insert and express in host organisms regulatory genes such as genes for inducers, repressors or enzymes which intervene by their enzymatic activity in the regulation, or one or more or all genes of a biosynthetic pathway. These genes can be heterologous or homologous in origin. The inserted genes may have their own promoter or else be under the control of the promoter of the sequence SEQ ID No. 1 or its homologs.

The gene construct advantageously comprises, for expression of the other genes present, additionally 3' and/or 5' terminal regulatory sequences to enhance expression, which are selected for optimal expression depending on the selected host organism and gene or genes.

These regulatory sequences are intended to make specific expression of the genes and protein expression possible as mentioned above. This may mean, depending on the host organism, for example that the gene is expressed or overexpressed only after induction, or that it is immediately expressed and/or overexpressed.

The regulatory sequences or factors may moreover preferably have a beneficial effect on expression of the introduced genes, and thus increase it. It is possible in this way for the regulatory elements to be enhanced advantageously at the transcription level by using strong transcription signals such as promoters and/or enhancers. However, in addition, it is also possible to enhance translation by, for example, improving the stability of the mRNA.

In addition the inventive gene construct preferably comprises additional gene of different biochemical pathways for example genes for the synthesis of vitamins, carotinoids, sugars such as monosaccharides, oligosaccharides or polysaccharides or fatty acid biosynthesis genes, more preferably the gene construct comprises fatty acid biosynthesis genes such as desaturases, hydroxylases, Acyl-ACP-thioesterases, elongases, acetylenases, synthesases or reductases such as n19-, n17-, n15-, n12-, n9-, n8-, n6-, n5-, n4-desaturases, hydroxylases, elongases, n12-acetylenase, Acyl-ACP-thioesterasen, β-Ketoacyl-ACP-synthases or β-Ketoacyl-ACP-reductases.

According to a yet further aspect of the invention there is provided a vector comprising the nucleic acid of the present invention or a gene construct of the present invention.

This aspect of the invention pertains to vectors, preferably expression vectors, containing a nucleic acid encoding a fatty acid transporter (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise at least one inventive nucleic acid or at least one inventive gene construct of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence are fused to each other so that both sequences fulfil the proposed function addicted to the sequence used. (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990) or see: Gruber and Crosby, in: Methods in Plant Molecular Biology and Biotechnolgy, CRC Press, Boca Raton, Fla., eds.: Glick and Thompson, Chapter 7, 89-108 including the references therein. Regulatory sequences include those which direct constitutive expression of a nucleotide sequence in many types of host cell and those which direct expression of the nucleotide sequence only in certain host cells or under certain conditions. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., fatty acid transporters, mutant forms of fatty acid transporters, fusion proteins, etc.).

The recombinant expression vectors of the invention can be designed for expression of fatty acid transporters in prokaryotic or eukaryotic cells, preferably in eukaryotic cells. For example, fatty acid transporter genes can be expressed in bacterial cells such as *C. glutamicum*, insect cells (using baculovirus expression vectors), yeast and other fungal cells (see Romanos, M. A. et al. (1992) Foreign gene expression in yeast: a review, Yeast 8: 423-488; van den Hondel, C. A. M. J. J. et al. (1991) Heterologous gene expression in filamentous fungi, in: More Gene Manipulations in Fungi, J. W. Bennet & L. L. Lasure, eds., p. 396-428: Academic Press: San Diego; and van den Hondel, C. A. M. J. J. & Punt, P. J. (1991) Gene transfer systems and vector development for filamentous fungi, in: Applied Molecular Genetics of Fungi, Peberdy, J. F. et al., eds., p. 1-28, Cambridge University Press: Cambridge), algae (Falciatore et al., 1999, Marine Biotechnology. 1, 3:239-251), ciliates of the types: *Holotrichia*, Peritrichia, Spirotrichia, Suctoria, *Tetrahymena, Paramecium, Colpidium, Glaucoma, Platyophrya, Potomacus, Pseudocohnilembus, Euplotes, Engelmaniella*, and *Stylonychia*, especially of the genus *Stylonychia lemnae* with vectors following a transformation method as described in WO9801572 and multicellular plant cells (see Schmidt, R.

and Willmitzer, L. (1988), High efficiency *Agrobacterium tumefaciens*-mediated transformation of *Arabidopsis thaliana* leaf and cotyledon explants, Plant Cell Rep.: 583-586); Plant Molecular Biology and Biotechnology, C Press, Boca Raton, Fla., chapter 6/7, S.71-119 (1993); F. F. White, B. Jenes et al., Techniques for Gene Transfer, in: Transgenic Plants, Vol. 1, Engineering and Utilization, eds.: Kung und R. Wu, Academic Press (1993), 128-43; Potrykus, Annu. Rev. Plant Physiol. Plant Molec. Biol. 42 (1991), 205-225 (and references cited therein) or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out with vectors containing constitutive or inducible promoters directing the expression of either fusion or non-fusion proteins. Fusion vectors add a number of amino acids to a protein encoded therein, usually to the amino terminus of the recombinant protein but also to the C-terminus or fused within suitable regions in the proteins. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the fatty acid transporter is cloned into a pGEX expression vector to create a vector encoding a fusion protein comprising, from the N-terminus to the C-terminus, GST-thrombin cleavage site-X protein. The fusion protein can be purified by affinity chromatography using glutathione-agarose resin. Recombinant fatty acid transporter unfused to GST can be recovered by cleavage of the fusion protein with thrombin.

Examples of suitable inducible non-fusion *E. coli* expression vectors include pTrc (Amann et al., (1988) Gene 69:301-315) and pET 11d (Studier et al., Gene Expression Technology Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21 (DE3) or HMS174(DE3) from a resident 1 prophage harboring a T7 gn1 gene under the transcriptional control of the lacUV 5 promoter.

Other vectors which are useful in prokaryotic organisms are known by a person skilled in the art such vectors are for example in *E. coli* pLG338, pACYC184, pBR-series such as pBR322, pUC-series such as pUC18 or pUC19, M113 mp-series, pKC30, pRep4, pHS1, pHS2, pPLc236, pMBL24, pLG200, pUR290, pIN-III113-B1, lgt11 or pBdCI, in *Streptomyces* pIJ101, pIJ364, pIJ702 or pIJ361, in *Bacillus* pUB110, pC194 or pBD214, in *Corynebacterium* pSA77 or pAJ667.

One strategy to maximize recombinant protein expression is to express the protein in a host bacteria with an impaired capacity to proteolytically cleave the recombinant protein (Gottesman, S., Gene Expression Technology: Methods in Enzymology 185, Academic Press, San Diego, Calif. (1990) 119-128). Another strategy is to alter the nucleic acid sequence of the nucleic acid to be inserted into an expression vector so that the individual codons for each amino acid are those preferentially utilized in the bacterium chosen for expression, such as *C. glutamicum* (Wada et al. (1992) Nucleic Acids Res. 20:2111-2118). Such alteration of nucleic acid sequences of the invention can be carried out by standard DNA synthesis techniques.

In another embodiment, the fatty acid transporter expression vector is a yeast expression vector. Examples of vectors for expression in yeast *S. cerivisae* include pYepSec1 (Baldari, et al., (1987) Embo J. 6:229-234), pMFa (Kurjan and Herskowitz, (1982) Cell 30:933-943), pJRY88 (Schultz et al., (1987) Gene 54:113-123), and pYES2 (Invitrogen Corporation, San Diego, Calif.). Vectors and methods for the construction of vectors appropriate for use in other fungi, such as the filamentous fungi, include those detailed in: van den Hondel, C. A. M. J. J. & Punt, P. J. (1991) "Gene transfer systems and vector development for filamentous fungi, in: Applied Molecular Genetics of Fungi, J. F. Peberdy, et al., eds., p. 1-28, Cambridge University Press: Cambridge or in: More Gene Manipulations in Fungi [J. W. Bennet & L. L. Lasure, eds., p. 396-428: Academic Press: San Diego]. Additional useful yeast vectors are for example 2 mM, pAG-1, YEp6, YEp 13 or pEMBLYe23.

Alternatively, the fatty acid transporter of the invention can be expressed in insect cells using baculovirus expression vectors. Baculovirus vectors available for expression of proteins in cultured insect cells (e.g., Sf 9 cells) include the pAc series (Smith et al. (1983) Mol. Cell. Biol. 3:2156-2165) and the pVL series (Lucklow and Summers (1989) Virology 170: 31-39).

The above mentioned vectors are only a small overview of possible useful vectors. Additional plasmids are well known by the skilled artisan and are described for example in: Cloning Vectors (Eds. Pouwels P. H. et al. Elsevier, Amsterdam-New York-Oxford, 1985, ISBN 0 444 904018).

In another embodiment, the fatty acid transporter of the invention may be expressed in unicellular plant cells (such as algae) see Falciatore et al., 1999, Marine Biotechnology. 1 (3):239-251 and references therein and plant cells from higher plants (e.g., the spermatophytes, such as crop plants). Examples of plant expression vectors include those detailed in: Becker, D., Kemper, E., Schell, J. and Masterson, R. (1992) "New plant binary vectors with selectable markers located proximal to the left border", Plant Mol. Biol. 20: 1195-1197; and Bevan, M. W. (1984) "Binary *Agrobacterium* vectors for plant transformation, Nucl. Acid. Res. 12: 8711-8721; Vectors for Gene Transfer in Higher Plants; in: Transgenic Plants, Vol. 1, Engineering and Utilization, eds.: Kung und R. Wu, Academic Press, 1993, S. 15-38.

A plant expression cassette preferably contains regulatory sequences capable to drive gene expression in plants cells and which are operably linked so that each sequence can fulfil its function such as termination of transcription such as polyadenylation signals. Preferred polyadenylation signals are those originating from *Agrobacterium tumefaciens* t-DNA such as the gene 3 known as octopine synthase of the Ti-plasmid pTiACH5 (Gielen et al., EMBO J. 3 (1984), 835 ff) or functional equivalents thereof but also all other terminators functionally active in plants are suitable.

As plant gene expression is very often not limited on transcriptional levels a plant expression cassette preferably contains other operably linked sequences like translational enhancers such as the overdrive-sequence containing the 5'-untranslated leader sequence from tobacco mosaic virus enhancing the protein per RNA ratio (Gallie et al 1987, Nucl. Acids Research 15:8693-8711).

Plant gene expression has to be operably linked to an appropriate promoter conferring gene expression in a timely, cell or tissue specific manner. Preferred are promoters driving constitutitive expression (Benfey et al., EMBO J. 8 (1989) 2195-2202) like those derived from plant viruses like the 35S CAMV (Franck et al., Cell 21 (1980) 285-294), the 19S CaMV (see also U.S. Pat. No. 5,352,605 and WO 84/02913) or plant promoters like those from Rubisco small subunit described in U.S. Pat. No. 4,962,028. Additionally vATPase-gene promoters such as an 1153 basepair fragment from Beta-vulgaris (Plant Mol Biol, 1999, 39:463-475) can be used to drive ASE gene expression alone or in combination with other PUFA biosynthesis genes.

Other preferred sequences for use operable linkage in plant gene expression cassettes are targeting-sequences necessary to direct the gene-product in its appropriate cell compartment (for review see Kermode, Crit. Rev. Plant Sci. 15, 4 (1996), 285-423 and references cited therein) such as the vacuole, the nucleus, all types of plastids like amyloplasts, chloroplasts, chromoplasts, the extracellular space, mitochondria, the endoplasmic reticulum, oil bodies, peroxisomes and other compartments of plant cells.

Plant gene expression can also be facilitated via a chemically inducible promoter (for review see Gatz 1997, Annu. Rev. Plant Physiol. Plant Mol. Biol., 48:89-108). Chemically inducible promoters are especially suitable if gene expression is wanted to occur in a time specific manner. Examples for such promoters are a salicylic acid inducible promoter (WO 95/19443), a tetracycline inducible promoter (Gatz et al., (1992) Plant J. 2, 397-404) and an ethanol inducible promoter (WO 93/21334).

Also promoters responding to biotic or abiotic stress conditions are suitable promoters such as the pathogen inducible PRP1-gene promoter (Ward et al., Plant. Mol. Biol. 22 (1993), 361-366), the heat inducible hsp80-promoter from tomato (U.S. Pat. No. 5,187,267), cold inducible alpha-amylase promoter from potato (WO 96/12814) or the wound-inducible pinII-promoter (EP-A-0 375 091).

Especially those promoters are preferred which confer gene expression in tissues and organs where lipid and oil biosynthesis occurs in seed cells such as cells of the endosperm and the developing embryo. Suitable promoters are the napin-gene promoter from rapeseed (U.S. Pat. No. 5,608,152), the USP-promoter from *Vicia faba* (Baeumlein et al., Mol Gen Genet, 1991, 225 (3):459-67), the oleosin-promoter from *Arabidopsis* (WO 98/45461), the phaseolin-promoter from *Phaseolus vulgaris* (U.S. Pat. No. 5,504,200), the Bce4-promoter from *Brassica* (WO 91/13980) or the legumin B4 promoter (LeB4; Baeumlein et al., 1992, Plant Journal, 2 (2):233-9) as well as promoters conferring seed specific expression in monocot plants like maize, barley, wheat, rye, rice etc. Suitable promoters to note are the lpt2 or lpt1-gene promoter from barley (WO 95/15389 and WO 95/23230) or those described in WO 99/16890 (promoters from the barley hordein-gene, the rice glutelin gene, the rice oryzin gene, the rice prolamin gene, the wheat gliadin gene, wheat glutelin gene, the maize zein gene, the oat glutelin gene, the *Sorghum* kasirin-gene, the rye secalin gene).

Also especially suited are promoters that confer plastid-specific gene expression as plastids are the compartment where precursors and some end products of lipid biosynthesis are synthesized. Suitable promoters such as the viral RNA-polymerase promoter are described in WO 95/16783 and WO 97/06250 and the clpP-promoter from *Arabidopsis* described in WO 99/46394.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

Vector DNA can be introduced into prokaryotic or eukaryotic cells via conventional transformation or transfection techniques. As used herein, the terms "transformation" and "transfection", conjugation and transduction are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, natural competence, chemical-mediated transfer, or electroporation. Suitable methods for transforming or transfecting host cells including plant cells can be found in Sambrook, et al. (Molecular Cloning: A Laboratory Manual. 2nd, ed., Cold Spring Harbor Laboratory, Cold Spring Harbor Laboratory Press, Cold Spring Harbor, N.Y., 1989) and other laboratory manuals such as Methods in Molecular Biology, 1995, Vol. 44, *Agrobacterium* protocols, ed: Gartland and Davey, Humana Press, Totowa, N.J.

The vector is introduced into a microorganism or plant cell (e.g., via *Agrobacterium* mediated gene transfer, biolistic transformation, polyethyleneglycol or other applicable methods) and cells in which the introduced ASE gene has homologously recombined with the endogenous fatty acid transporter gene are selected, using art-known techniques. In case of plant cells the AHAS gene described in Ott et al., J. Mol. Biol. 1996, 263:359-360 is especially suitable for marker gene expression and resistance towards imidazolinone or sulphonylurea type herbicides.

In another embodiment, recombinant organisms such as microorganisms can be produced which contain selected systems which allow for regulated expression of the introduced gene. For example, inclusion of a fatty acid transporter gene on a vector placing it under control of the lac operon permits expression of the fatty acid transporter gene only in the presence of IPTG. Such regulatory systems are well known in the art. Recombinant organisms means an organism which comprises an inventive nucleic acid sequence, a gene construct or a vector in the cell or inside the genome at an place which is not the "natural" place or an the "natural" place but modified in a manner which is not the natural manner that means the coding sequence is modified and/or the regulatory sequence is modified. Modified means that a single nucleotide or one or more codons are changed in comparison to the natural sequence.

A host cell of the invention, such as a prokaryotic or eukaryotic host cell in culture, can be used to produce (i.e., express) a fatty acid transporter. An alternate method can be applied in addition in plants by the direct transfer of DNA into developing flowers via electroporation or *Agrobacterium* medium gene transfer. Accordingly, the invention further provides methods for producing fatty acid transporters using the host cells of the invention. In one embodiment, the method comprises culturing the host cell of invention (into which a recombinant expression vector encoding a fatty acid transporter has been introduced, or into which genome has been introduced a gene encoding a wild-type or altered fatty acid transporter) in a suitable medium until fatty acid transporter is produced. In another embodiment, the method further comprises isolating fatty acid transporters from the medium or the host cell.

Host organisms suitable in principle to cover the nucleic acid of the invention, the novel gene construct or the inventive vector are all prokaryotic or eukaryotic organisms. The host organisms advantageously used are organisms such as bacteria, fungi, yeasts, animal or plant cells. Additional advantageously organisms are Fungi, yeasts or plants, preferably fungi or plants, very particularly preferably plants such as oilseed plants containing high amounts of lipid compounds such as rapeseed, primrose, canola, peanut, linseed, soybean, sufflower, sunflower, borage or plants such as maize, wheat, rye, oat, triticale, rice, barley, cotton, manihot, pepper, tagetes, solanaceaous plants such as potato, tobacco, eggplant, and tomato, Vicia species, pea, alfalfa, bushy plants (coffee, cacao, tea), Salix species, trees (oil palm, coconut) and perennial grasses and forage crops. Particularly preferred plants of the invention are oilseed plants such as soybean, peanut, rapeseed, canola, sunflower, safflower, trees (oil palm, coconut).

According to a further aspect of the invention there is provided a nucleic acid molecule comprising SEQ ID NO:1 or a part thereof, or homologue thereof, which encodes a peroxisomal ABC (ATP-binding Cassette) transporter.

Also provided is a nucleic acid encoding an ABC cassette transporter protein especially one involved in fatty acid transport across peroxisomal membranes, the nucleic acid being selected from a group consisting of:

(a) DNA having the nucleotide sequence given herein in SEQ ID NO:1 which encodes a protein having the amino acid sequence given herein as SEQ ID NO:2.

(b) nucleic acid which hybridize to DNA of (a) above (e.g. under stringent conditions); and (c) nucleic acids which differ from the DNA of (a) or (b) above due to the degeneracy of the genetic code, and which encodes a protein encoded by a DNA of (a) or (b) above.

DNAs of the present invention include those coding for proteins homologous to, and having essentially the same biological properties as, the proteins disclosed herein, and particularly the DNA disclosed herein as SEQ ID NO:1 and encoding the protein given herein SEQ ID NO:2. This definition is intended to encompass natural allelic variations therein. Thus, isolated DNA or cloned genes of the present invention can be of any plant species of origin. Thus, DNAs which hybridise to DNA disclosed herein as SEQ ID NO:1 (or fragments or derivatives thereof which serve as hybridisation probes as discussed below) and which code on expression for a protein associated with fatty acid or acyl CoA transport into peroxisomes (e.g., a protein according to SEQ ID NO:2) are included in the present invention.

According to a further aspect of the present invention there is provided use of the nucleic acid of the invention and/or protein or polypeptide encoded thereby in any one or more of the following processes: regulating fatty acid transport across peroxisome and/or glyoxisome membranes; regulating growth; regulating seed development and; modulating fatty acid utilisation by the plant.

According to a yet further aspect of the present invention there is provided a method of regulating any one or more of the following processes: regulating fatty acid transport across peroxisome and/or glyoxisome membranes; regulating growth; regulating seed development and; modulating fatty acid utilisation by the plant comprising genetically engineering a plant cell or tissue or seed so as to enhance or reduce/prevent expression of the nucleic acid of the present invention.

Such techniques are well-known in the art and include but are not restricted to: reduction of expression of the nucleic acid and encoded protein by antisense expression of part or all of the sequence corresponding to SEQ ID No1; expression of part or all of SEQ ID No1 as double stranded interference RNA (RNAi); or co-supression of the endogenous gene brought about by introduction of additional copies of part or all of SEQ ID No1. Conversely expression may be increased, or altered spatially and temporally, by the introduction of constructs fused to different regulatory sequences as hereinbefore described.

According to a yet further aspect of the invention there is provided a method of modification of a plant cell to increase or decrease the transport of some or all fatty acids across cell membranes and/or to increase or prevent their breakdown.

Preferably the modification could take the form of mutating, disabling or deleting the CTS gene. The CTS gene could also be modified to alter its expression levels in specific tissues or at specific times. By example and not by way of limitation, CTS expression could be inhibited in developing seeds but not in germinating seeds. Alternatively, the plant cell may be modified so as to containing an increased number of copies of the nucleic acid according to the invention as compared to the wild-type.

Mutation of the sequence may be through designed changes or random changes followed by selection to introduce variants of SEQ ID No 1 and SEQ ID No2 with altered substrate specificity or transport rate or regulation, or through the expression of mutants with dominant negative activity.

The invention therefore includes transgenic plants comprising a nucleic acid molecule of the invention as well as transgenic plants adapted to increase or decrease expression of an active peroxisomal ABC transporter, for example by having increased or decreased numbers of gene copies or modification of transcription control elements According to a yet further aspect of the invention there is provided a method of regulating fatty acid levels in plants comprising genetically engineering a plant cell or tissue or seed so as to disrupt, deactivate, disable, mutate, delete, knockout or render transcriptionally ineffective a nucleic acid according to the invention.

According to a yet further aspect of the invention there is provided a plant cell and/or a plant tissue and/or plant and/or plant seed that does not containing a transcriptionally activated/activatable form of the nucleic acid molecule according to the invention or contains a reduced number of copies of the nucleic acid of the present invention as compared to the wild-type.

According to a yet further aspect of the invention there is provided a plant generated from a plant cell and/or plant tissue and/or plant and/or plant seed which contains a disrupted, deactivated, disabled, mutated, deleted, knocked-out or rendered transcriptionally ineffective nucleic acid according to the invention as compared to the wild-type.

According to a yet further aspect of the invention there is provided a plant cell and/or a plant tissue and/or plant and/or plant seed comprising:

(i) an increased number of copies of the nucleic acid according to the invention as compared to the wild-type;
(ii) increased transcription of the nucleic acid according to the invention as compared to the wild-type; or
(iii) a differing number of copies of the nucleic acid according to the invention depending on the time of development of the plant.

According to a yet further aspect of the invention there is provided a plant generated from a plant cell and/or plant tissue and/or plant and/or plant seed comprising:
(i) an increased number of copies of the nucleic acid according to the invention as compared to the wild-type;
(ii) increased transcription of the nucleic acid according to the invention as compared to the wild-type; or
(iii) a differing number of copies of the nucleic acid according to the invention depending on the time of development of the plant.

According to a yet further aspect of the invention there is provided a primer comprising any one of SEQ ID NOS: 3 to 10 or parts thereof capable of recognising the nucleic acid of the present invention or homologues thereof, the primer being specific for a nucleic acid according to the invention.

The following T-DNA knockout lines containing insertions in the CTS gene were screened from Wisconsin knockout population alpha:— cts-2; position of insertion in genomic DNA is 16,674 in Accession AL161596 (*Arabidopsis thaliana* DNA chromosome 4, contig fragment No. 92, VERSION AL161596.2). This corresponds to Exon 3 of the gene or position 846 in Sequence ID NO:1 (cDNA) and in codon Thr115 in SEQ ID NO:2 (the derived amino acid sequence). The primers used in the initial PCR screen are preferably H1A6T7 DSR1 (SEQ ID NO:8) AND JL 202 (SEQ ID NO:11).

F27; position of insertion in genomic DNA is 15,873 in Accession AL161596. This is in Intron-1 which is located in the 5'-UTR. The primers used in the initial PCR screen are preferably H1A6T7 DSF1 (SEQ ID NO:4) and JL 202 (SEQ ID NO:11).

F12; position of insertion in genomic DNA is 17,318 in Accession AL161596. This is in Intron-4. The primers used in the initial PCR screen are preferably H1A6T7 DSF1 (SEQ ID NO:4) and JL 202 (SEQ ID NO:11).

Preferably, the primers of the present invention include:
Primer H1A6T7 DSF1 Forward primer 5' at position 15,667 of Accession AL161596, (SEQ ID NO:4); Primer H1A6T7 DSF2 5' position at 15,640 of Accession AL161596, (SEQ ID NO:5); Primer H1A6T7 DSF3 5' position at 15,320 of Accession AL161596, (SEQ ID NO:6); Primer H1A6T7 DSF 5' position at 15,542 of Accession AL161596, (SEQ ID NO:3); Primer H1A6T7 DSR1Reverse primer 5' at position 20,611 of Accession AL161596, (SEQ ID NO:8); Primer H1A6T7 DSR2 5' position at 17,819 of Accession AL161596, (SEQ ID NO:9); Primer H1A6T7 DSR35' position at 21,191 of Accession AL161596, (SEQ ID NO:10); Primer H1A6T7 DSR 5' position at 19,978 of Accession AL161596 (SEQ ID NO:7) and/or; Primer JL 202 Left Border primer for PCR out of constructs of Wisconsin knockout population alpha (SEQ ID NO:11).

According to a yet further aspect of the invention there is provided use of a primer comprising any one of SEQ ID NOS: 3 to 10 or parts thereof capable of recognising the nucleic acid of the present invention or homologues thereof, in identifying a nucleic acid sequence according to the invention.

According to a yet further aspect of the invention there is provided a method of identifying plant material selected from a plant cell and/or plant tissue and/or plant and/or plant seed comprising a disrupted, deactivated, disabled, mutated, deleted, knocked-out or rendered transcriptionally ineffective nucleic acid according to the invention comprising contacting the plant material with a primer comprising any one of SEQ ID NOS: 3 to 10.

BRIEF DESCRIPTION OF THE FIGURES

FIG. 1 illustrates alignment of peroxisomal ABC transporters. The peptide sequences of Human ALD (SEQ ID NO:16) and PMP70 (SEQ ID NO:17) were aligned with *Arabidopsis* CTS (SEQ ID NO 18 and SEQ ID NO:19) and yeast Pxa1 (SEQ ID NO:20), and yeast CTS (SEQ ID NO:21). Although the *arabidopsis* ABC is a double transporter consisting of 2 sets of transmembrane domains comprising multiple transmembrane helices and 2 ATPase domains (format: TM domain-ATPase-TM domain-ATPase) its closest homologs outside the plant kingdom are half transporters (format: TM domain-ATPase). For this alignment the peptide sequence of the *Arabidopsis* abc was arbitrarily divided into two halves: CTSa and CTSb. Conserved domains previously described in the literature are highlighted. Loop 1 is conserved among peroxisomal ABC transporters only. The EAA-like motif, Walker A and B, and the C-sequence are all conserved between prokaryotic and eukaryotic ABC transporters.

FIG. 6 illustrates the isolation of individual CTS knockout plants. 100 individual plants were screened by PCR for the exon 2 knockout (cts-2) from a pool containing seed from 9 T-DNA tagged lines previously identified by PCR. PCR was carried out using a T-DNA specific primer (JL-202) and gene-specific primer DSR1 (A) or DSR3 (B). A positive plant (lane 5) was identified from this sample of 15 individuals. (C) HindIII restriction digest of genomic DNA from wt (lane 1) and the positive plant (lane 2) was probed with CTS probe. Bands of 2.5 kb and 6.5 kb correspond to predicted sizes for wt CTS. The band of 8.7 kb corresponds to a predicted size consistent with a T-DNA insertion in exon 2. Together these data suggest that the positive plant is a heterozygote having one copy of the wt CTS gene and a mutant gene containing a T-DNA insertion. (D) PCR identifying presence of knockout plants in a pool of germinating seedlings from 9 T-DNA tagged lines for knockout F27 (lanes 1-3) and knockout F12 (lanes 4-6) using a T-DNA specific primer and a range of gene-specific primers.

FIG. 8a illustrates the profiles of triacyl glycerol-derived fatty acids and acyl CoA levels in wild type and cts-2 mutant by comparison of TAG-derived fatty acids in the wild types and cts-2 mutant in seeds and seedlings 0, 2 and 5 days after sowing.

FIG. 8b illustrates the profiles of triacyl glycerol-derived fatty acids and acyl CoA levels in wild type and cts-2 mutant by a profile of TAG-derived fatty acids in imbibed wild type and mutant seeds by chain length at 0 days after sowing.

FIG. 8c illustrates the profiles of triacyl glycerol-derived fatty acids and acyl CoA levels in wild type and cts-2 mutant by a profile of TAG-derived fatty acids in imbibed wild type and mutant seeds by chain length at 5 days after sowing.

FIG. 8d illustrates the profiles of triacyl glycerol-derived fatty acids and acyl CoA levels in wild type and cts-2 mutant by comparison of Acyl CoA levels in wild types and cts-2 mutant seedlings 0, 2 and 5 days after sowing.

FIG. 8e illustrates the profiles of triacyl glycerol-derived fatty acids and acyl CoA levels in wild type and cts-2 mutant by a profile of Acyl CoAs in imbibed wild type and mutant seeds by chain length at 0 days after sowing.

FIG. 8f illustrates the profiles of triacyl glycerol-derived fatty acids and acyl CoA levels in wild type and cts-2 mutant by a profile of Acyl CoAs in imbibed wild type and mutant seeds by chain length at 5 days after sowing.

DETAILED DESCRIPTION OF THE INVENTION

The yeast and human peroxisomal ABC transporter proteins were used to search the publically accessible sequence databases of *Arabidopsis thaliana* using the BLAST Algorithm. One sequence was identified (T5J17.20; AT4G39850, from chromosome IV) which had a significant sequence homology to all the probe sequences and which corresponded to an EST (H1A6T7) from a 3 day seedling hypocotyl library. This clone was obtained from the *Arabidopsis* Biological Resource Centre at Ohio State University (USA), fully sequenced and named CTS (SEQ ID NO:1).

Figure 1:
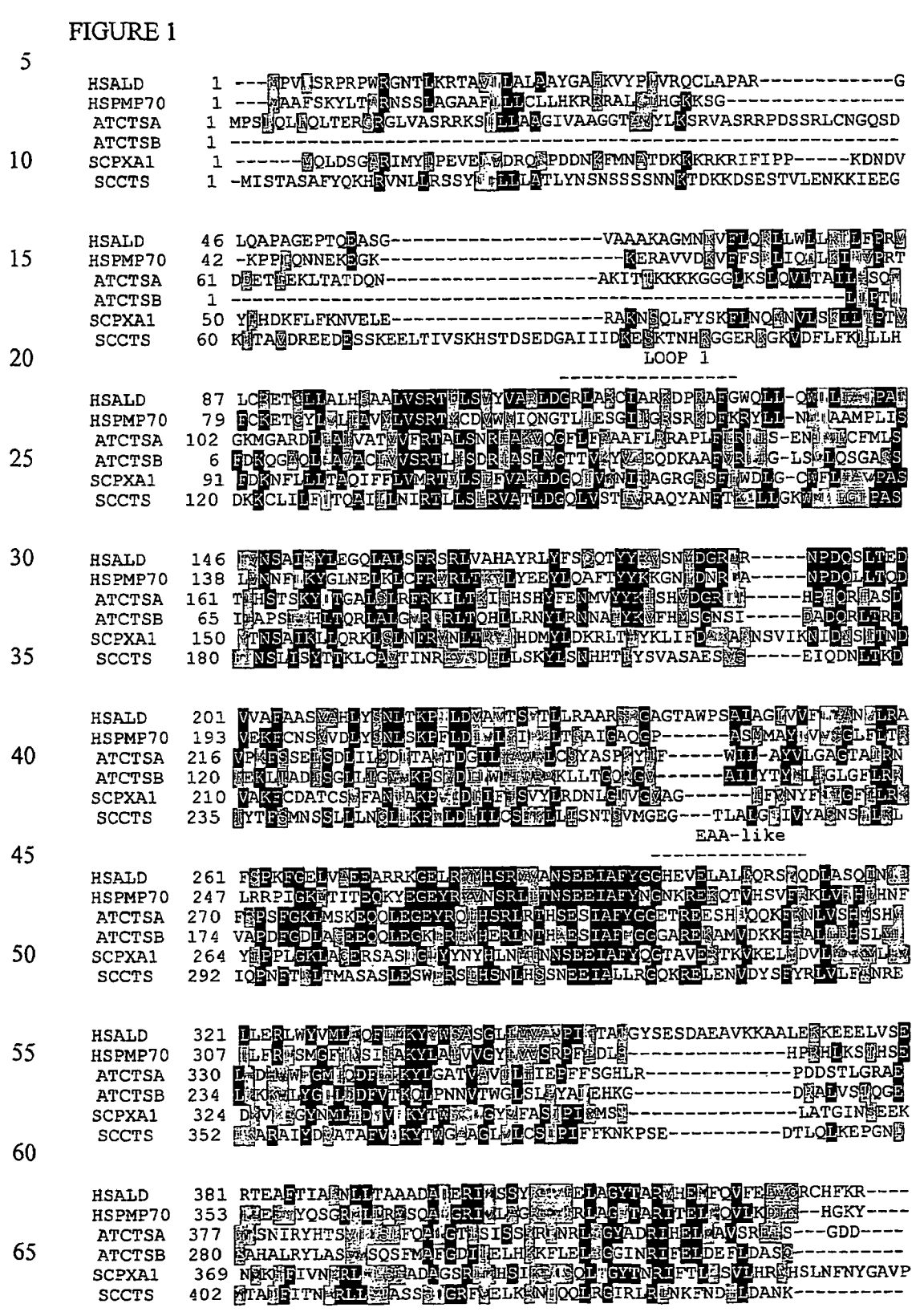

Bioinformatic analysis of the sequence revealed that this encoded a protein of 1337 amino acids with a predicted molecular weight of 149,576 (SEQ ID NO:2). Functional ABC transporters have 4 domains, two sets of 5 or 6 transmembrane spans and two ATPase domains which can be on separate polypeptide chains or fused in various combinations. CTS is of the type in which all domains are fused where as ScPxa2p is of the half transporter type containing one transmembrane domain and one ATPase domain. CTS contains all the conserved residues typical of an ABC transporter. The two half transporter domains of CTS are 34% identical to one another. The highest matches on BLASTp search (P<7.1 e-67) are the mammalian PMP70 and adrenoleukodystrophy proteins, also half transporters that are involved in fatty acid transport into peroxisomes. *Saccharomyces cerevisiae* Pxa2p is the 6th most similar sequence (P=1.5e-44). An alignment of the deduced amino acid sequences of CTS with PMP70, ALDP, ScPxa1p and ScPxa2p is shown in FIG. 1. The ATP binding sites, designated Walker A and B motifs are highly conserved in all ATPases. The C-sequence, otherwise known as the ABC motif is diagnostic of the ABC transporter superfamily, as is the EAA sequence. The sequence NSEEIAFY (SEQ ID NO:12) is diagnostic of the human and yeast peroxisomal ABC transporters and the closely related sequence H(S/A)SIAF(Y/F) (SEQ ID NO:13) occurs in the two halves of CTS. The loop1 region and the sequence PQRPYMTLGTLRDQ (SEQ ID NO:14) is diagnostic of animal peroxisomal ABC transporters. The almost identical sequence PQRPY(M/T)(A/C)LGTLRDQ (SEQ ID NO:15) occurs in both halves of CTS. Therefore CTS contains sequences which assign it to the peroxisomal sub-class of ABC transporters.

Figure 2:
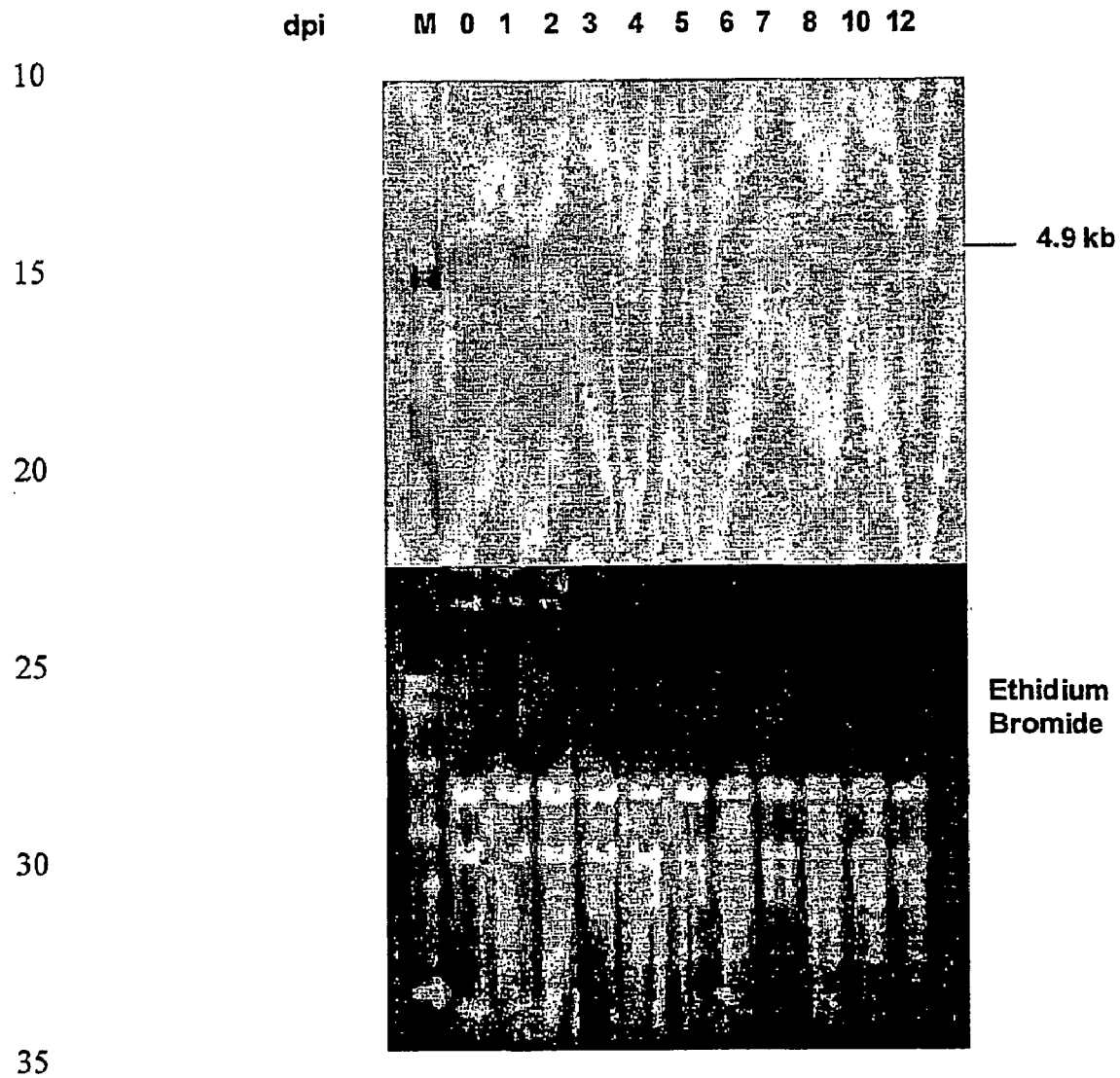
FIG. 2 illustrates analysis of CTS transcript levels during germination in the light. Seeds were surface sterilized using Milton® and imbibed in the dark at 4 C for 4 d before plating and incubating at 22 C Data points are days post imbibition (dpi).

To determine whether the expression pattern of CTS was consistent with its involvement in fatty acid uptake in peroxisomes, a northern blot was performed (FIG. 2). Fatty acid oxidation is an on-going process in plant cells due to turn over of membrane lipids by β-oxidation. However higher levels of expression would be expected during and immediately after germination as is seen for the β-oxidation enzymes thiolase (Germain et al., 2001) and acyl CoA oxidase (Hooks et al., 1999). Consistent with this the CTS probe detects a transcript of 4.9 kb that is expressed throughout the first 12 days post imbibition but with highest expression at day 1.

Figure 3:
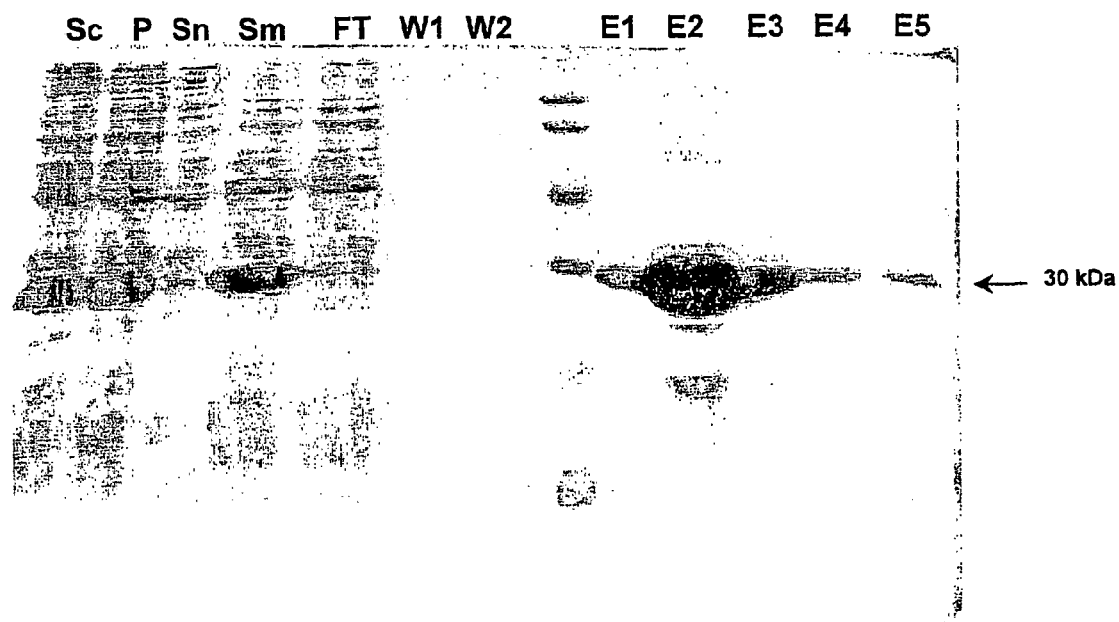
FIG. 3 shows expression and purification of second ATPase domain of CTS.
Figure 4:
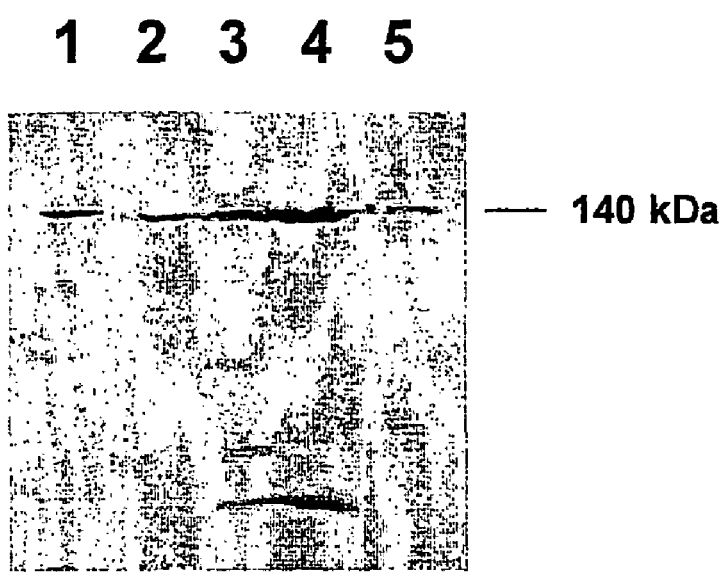
FIG. 4 illustrates the location of CTS to membrane fractions. *Arabidopsis* cell suspension culture derived from leaf was homogenized and centrifuged at low speed (1000 g) to remove nuclei followed by 20 000 g to sediment membrane fractions. These were then resuspended and loaded onto a sucrose step gradient. Fractions of equivalent protein loading were separated by SDS-PAGE followed by immuno-blotting with antisera raised against CTS. Lane 1, SDS-extraction of original homogenate; lane 2, post-nuclear supernatant; lane 3, resuspended membrane pellet; lane 4, membrane recovered at 0.5M/1.6M sucrose interface and lane 5, 1.6M/2.2M sucrose interface. Concentration of CTS in the membrane fractions is consistent with CTS being a membrane protein.
Figure 7:
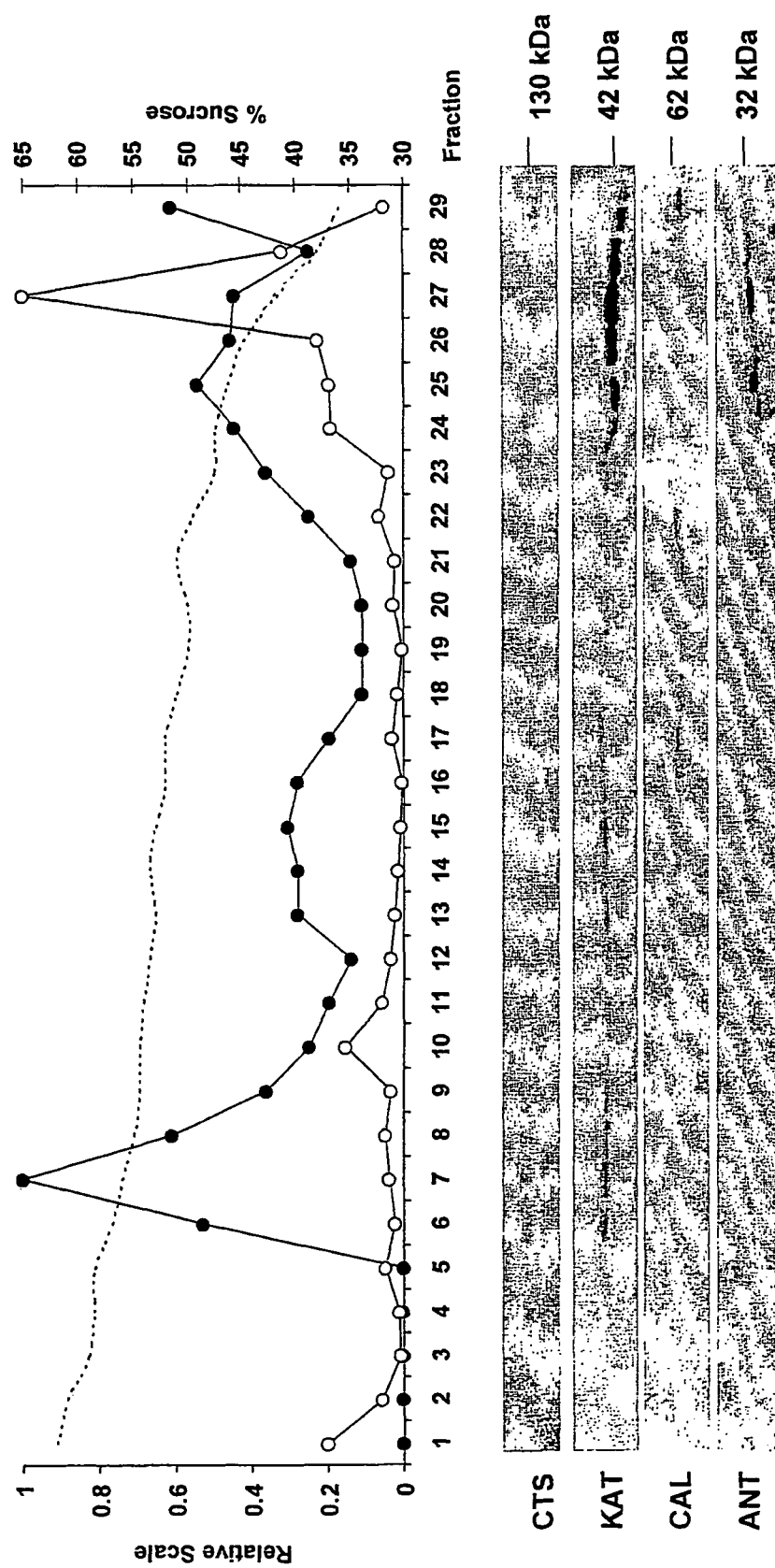
FIG. 7 illustrates CTS localisation in peroxisomes. Sucrose density gradient showing the localisation of peroxisomal markers catalase (closed circles) and 3-ketoacyl thiolase (KAT), ER marker calreticulin (CAL), mitochondrial marker adenine nucleotide translocator (ANT) and chlrophyll (open circles). CTS antigen follows the distribution of catalase and thiolase.

To provide experimental evidence for the peroxisomal location of CTS, antibodies were raised to the second ATPase domain. A fragment corresponding to amino acids 1112-1337 was cloned into pET28b (Novagen) to produce a his tagged recombinant protein. The recombinant protein, which is in inclusion bodies was purified by NTA agarose chromatography (FIG. 3). Affinity purified antisera detected a protein of ca.140 kDa in membrane fractions from *Arabidopsis* seedlings and tissue culture cells (FIG. 4). Further experiments demonstrated the localisation of this protein specifically in peroxisomes/glyoxysomes (FIG. 7).

Figure 5:
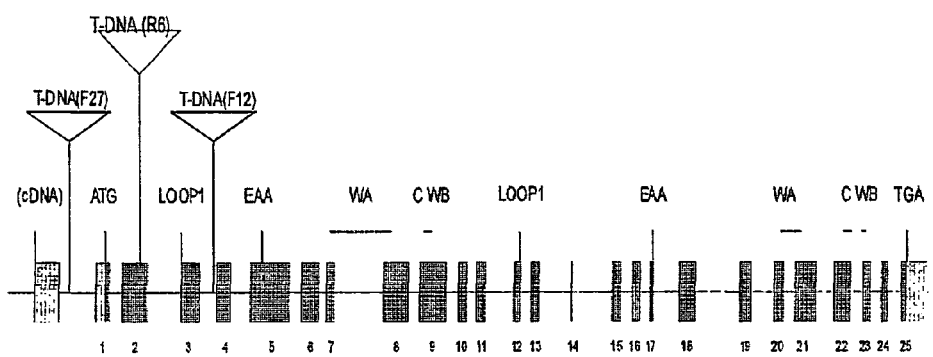
FIG. 5 represents the location of T-DNA insertions in three CTS knockouts cts-2F27 and F12. Exons are shown as dark shaded boxes. Non coding transcribed regions are indicated by light shading.
Figure 8:
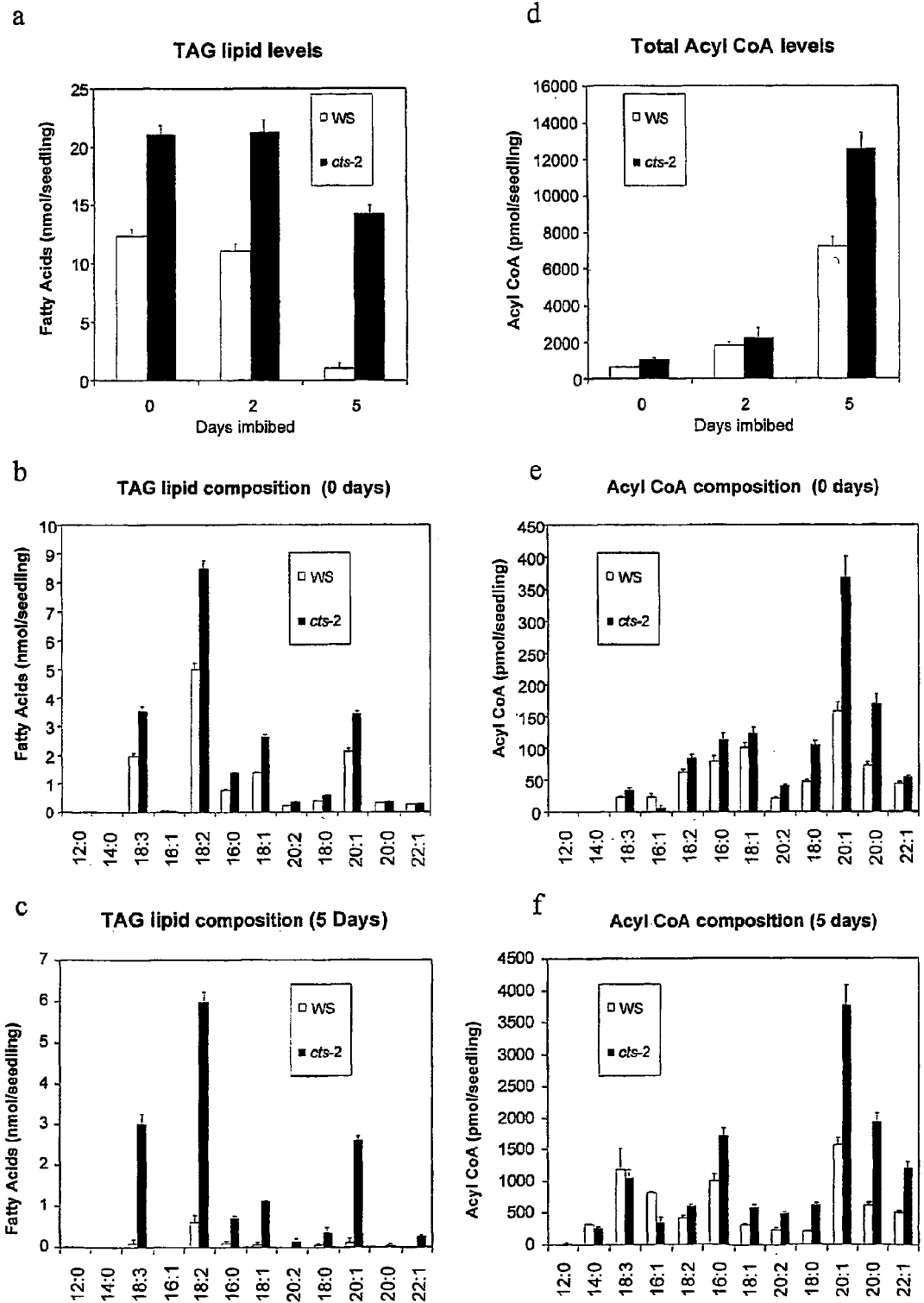
FIG. 8 illustrates the profiles of triacyl glycerol-derived fatty acids and acyl CoA levels in wild type and cts-2 mutant.

Thus far the function of the CTS protein is inferred from sequence homology to known peroxisomal fatty acid ABC transporters. To obtain functional information for CTS knockout mutations in *Arabidopsis* were sought through reverse genetics. Primers were designed and sent to the *Arabidopsis* knock out facility at the University of Wisconsin (USA) to screen their population of T-DNA tagged mutants. Three alleles of CTS were detected (FIG. 5). The location of the T-DNA insertions were determined by sequencing the PCR products. T-DNA insertions are in exon 2 and introns 1 (in the 5'UTR) and 4 of CTS. The insertions in exon 2 of CTS would be predicted to be a null alleles, while those in the introns may or may not give a phenotype depending on whether they are correctly spliced out from the transcript. Single heterozygous plants have been obtained for each T-DNA insertion (FIG. 6). Heterozygous cts-2 plants were allowed to self fertilise and homozygous progeny selected. Homozygous seeds and seedlings were subjected to triacyl glycerol and acyl CoA profiling (FIG. 8). These results provide strong support for the proposed biochemical function of CTS as a fatty acyl CoA transporter.

Methods

The cts-2 mutant allele was obtained by PCR-based screening of the Wisconsin-alpha gene knockout lines for insertions in the CTS gene (Krysan et al., 1999). The sequence of the CTS RNA was obtained using the cDNA clone H1A6T7 (ABRC, Ohio State Univ.). Total RNA was extracted, separated by denaturing agarose gel electrophoresis and transferred to a hybridisation membrane. The membrane was hybridised with 32P-labelled clone H1A6T7 as described by Hooks et al., (1999) and detected by phophoimaging.

A polyclonal antibody was raised against a C-terminal fragment of CTS (amino acids 1112-1337) expressed in *E. coli* strain BL21(DE3)pLysS (Novagen) using a pET28b (Novagen) construct containing an NheI-BamHI fragment of cDNA clone H1A6T7 (EMBL accession AJ311341). The antibody was affinity-purified using the recombinant fragment (Tugal et al., 1999).

Acyl CoAs and total lipids were extracted from five replicate 3-10 mg tissue samples and analyzed according to Larson and Graham (2001). An aliquot of the total lipid extract was used for triacylglycerol (TAG) determination. A 1 mL 100 mg bed volume BOND ELUT® (Varian, Surrey, UK) SPE column was prepared by elution with 2×1 mL methanol, 3×1 mL hexane, and then 100 µL sample loaded in hexane. TAGs were eluted with 1.5 mL 2:3 (v/v) chloroform:hexane, dried under vacuum, transmethylated to fatty acid methyl esters, and analyzed as described previously (Larson and Graham, 2001). Specificity for TAG separation was optimized so that the diacylglycerol, dipalmitin (Sigma) was excluded from the SPE eluate.

To provide further information on the specific nature of the block in lipid breakdown and hence the function of the CTS protein, the levels of triacyl glycerol (TAG) and acyl CoAs were measured in the cts-2 mutant and corresponding WS wild type. All lines were germinated in the presence of 1% sucrose (and the testa of the cts-2 mutants was ruptured to allow germination) to ensure that seedlings were at similar morphological stages of development. The summed changes in fatty acid content of extracted TAG indicate similar levels of TAG-derived fatty acids in imbibed seeds of the wild type and mutant on day 0 (FIG. 8a). Higher apparent TAG levels per seed(ling) in the mutant reflects bigger seed size and is not seen when the data is expressed on a fresh weight basis). TAG fatty acid levels only declined slightly after 2 days germination even in wild type seedlings, presumably due to the presence of sucrose as an alternative energy source. However by day 5, TAG derived fatty acids had decreased by 95.8% in the wild types but by only 32.3% in the mutant. All TAG-derived fatty acid chain lengths were mobilised after 5 days germination for wild type, but the cts-2 mutant retained high levels of the same TAGs (FIGS. 8b,c).

Total Acyl CoAs increased in both lines over the period 0-5 days (FIG. 8d), but this is much more dramatic in the mutant. By day 5 some of the increase in both wild type and mutant seedlings may reflect new lipid synthesis (e.g. for membrane biogenesis). However the most striking observation is the retention of 20:1 and to a lesser extent 20:0 and 22:1 CoA's in seedlings of the cts-2 mutant (FIGS. 8e,f). As C20 fatty acids are only very minor components of non-storage lipids in *Arabidopsis*, these data demonstrate that there is a severe block in carbon flux from stored triacyl glycerols during germination in the mutant.

Analysis of TAG-derived fatty acids and acyl CoAs demonstrates that while some lipid is mobilised in the cts-2 mutant, catabolism is inhibited before β-oxidation, resulting in an increased acyl CoA pool. This is particularly pronounced for C20 and C22 acyl CoAs which are predominantly TAG-derived. These data argue strongly that the primary defect in the cts-2 mutant is in transport of fatty acyl CoAs into peroxisomes. 18:2 and 18:3 CoAs do not accumulate to a similar extent, which may reflect their use in the synthesis of structural lipids by ER mediated pathways. In contrast C20:1 is not a component of structural lipids and may accumulate because it lacks a synthetic sink route. It is possible that the accumulation of 20:1 CoA, or depletion of free coenzyme A results in the inhibition of lipolysis and therefore the release of further fatty acids from storage TAG. The accumulation of acyl CoAs argues that these are the substrates of the CTS protein, and suggests that unlike X-ALD patients CTS mutants retain VLCFA synthetase activity. The substantial accumulation of long and very long chain acyl CoA's in the cts-2 mutant is consistent with the activation of these fatty acids by acyl CoA synthetases on the cytoplasmic side of the peroxisomal membrane, as reported for *S. cerevisiae* (Hettema et al., 1996), mammals (Mannaerts et al., 1982) and plants (Olsen and Lusk 1994). The finding that all fatty acid chain lengths are mobilized in wild type and retained in the mutant argues that the transporter has broad substrate specificity with respect to acyl chain length. Acyl CoA's are amphipathic molecules, as are the substrates for many ABC transporters.

Oilseeds can be engineered to produce economically valuable unusual fatty acids. However, the exact fate of the unusual fatty acid, once it is made, is not known. What is known is that not enough of the valuable fatty acid ends up in seed oil. One factor that appears to limit novel oil yield is that the fatty acids comprising them are broken down before being incorporated into oil (Eccleston and Ohlrogge 1998). CTS, the nucleic acid of the present invention, is an excellent candidate to be involved at the beginning of this process. As indicated by the data in FIG. 8, mutating the function of CTS reduces or abolish the entry of some or all fatty acids into the glyoxisome/peroxisome and therefore prevent their breakdown. We predict this would allow their accumulation in seeds or other plant tissues. However, the plant still needs to be able to utilise endogenous fatty acids for germination and growth. Blocking β-oxidation through the mutation of thiolase results in germination but subsequent growth is dependent on exogenously supplied sucrose (Germain et al., 2001). It should be possible to alter the expression levels of CTS in specific tissues or at specific times, for example inhibiting its activity in developing seeds but not in germinating seeds. Alternatively if we can determine and then alter its substrate specificity we may be able to allow accumulation of desired novel oils but not prevent germination and seedling establishment using endogenous fatty acids. An additional problem is that when high levels of novel oils can be achieved, oilseeds cannot use these foreign oils as an efficient source of fuel for young seedlings to grow, resulting in non-viable seed. For example, expressing a form of CTS that cannot transport the novel oils in the developing seed but switching on a form which can use the novel oil as a substrate during germination might overcome this problem. These proteins with altered substrate specificity might arise as a resulted of targeted or random mutation of the gene followed by an appropriate selection, or the use of the *Arabidopsis* protein to isolate homologues which may have different substrate specificities from species which naturally accumulate high levels of the desired novel oils. Therefore the protein of the present invention has the potential to increase the accumulation of novel oils in seeds to economically viable levels.

Mutants in β-oxidation show resistance to 2,4-dichlorophenoxybutyric acid (2,4 DB, Hayashi et al., 1998 and indole-3-butyric acid (IBA, Zollman et al 2000) and β-oxidation is clearly impaired in the cts-2 mutant, most likely as a consequence of a defect in transport of fatty acyl CoAs into the peroxisome for metabolism. CTS maps to the same location on chromosome IV as the ped3 mutant (Hayashi et al., 1998). IBA and 2,4 DB are amphipathic molecules and CTS is a good candidate to mediate their uptake into peroxisomes. If a dominant negative or RNAi version of CTS could be expressed under the control of a regulated promoter, it could be used as a selectable marker for plant transformation. The expression of the dominant negative form of the protein would most likely confer resistance to IBA or 2,4 DB. Resistance results in a 'long root' phenotype and would allow plants expressing this marker to be selected on medium containing IBA or 2,4 DB, sucrose and the inducing molecule for the regulated promoter. The advantage is that the selectable marker is of plant origin and unlike, for example, herbicide resistance, confers selection only in the presence of three separate molecules which is not going to occur in nature. It does not confer antibiotic resistance, so there can be no danger of disseminating resistance in the environment. The use of a regulated promoter results in expression of the selection only under defined conditions.

REFERENCES

Footitt, S., Slocombe, S P., Laarner, V., Kurup, S., Wu, Y., Larson, T., Graham, I., Baker, A and Holdsworth (2002) EMBO 21, 12, 2912-2922.

Germain, V., Rylott, E. Larson, T. R., Sherson, S. M., Bechtold, N. Carde, J-P., Bryce J. H. Graham, I. A. and Smith, S. M. (2001) Plant J. 28, 1-12.

Hayashi M, Toriyama, K, Kondo, M. ad Nishimura, M. (1998) Plant Cell 10, 183-195.

Hettema, E. H., van Roermund, C W T, Distel, B. van den Berg, M. Vilela, C., Rodrigues-Pousada C, Wanders, R J A and Tabak, H F (1996) EMBO J. 15, 3813-3822.

Hooks, M. A., Kellas, F. and Graham, I. A. (1999) Plant J. 20, 1-3.

Krysan, P. J., Young, J. C. and Sussman, M. R. (1999) Plant Cell, 11, 2283-2290.

Larson, T. R., Graham, I. A. (2001) Plant J. 25:115-125

Mannaerts, G. P., van Veldhoven, P., van Broekhoven, A., Vandebroek, G., and Debeer, L. J. (1982). Biochem. J. 204, 17-23.

Mosser, J. Douar, A. M., Sarde, C-O., Kioschis, P. Feil, R. Moser, H., Poustka, A-M., Mandel, J-M. and Augbourg, P (1993) Nature 361, 726-730.

Olsen, J. A. and Lusk, K. R. (1994) Phytochemistry 36, 7-9.

Russell, L., Larner, V., Kurup, S., Bougourd and Holdsworth, M (2000) Development, 127, 3759-3767.

Tugal, H. B., Pool, M. and Baker, A. (1999) Plant Physiology, 120, 309-320.

Zollman B. K., Yoder, A. and Bartel, B. (2000) Genetics 156, 1323-1337

```
SEQUENCE LISTING

<160> NUMBER OF SEQ ID NOS: 11

<210> SEQ ID NO 1
<211> LENGTH: 5073
<212> TYPE: DNA
<213> ORGANISM: Arabidopsis thaliana

<400> SEQUENCE: 1
atgtgctgca aggcgattaa gttgggtaac gccagggttt tcccagtcac gacgttgtaa      60
aacgacggcc agtgaattgt aatacgactc actatagggc gaattgggta ccgggccccc     120
cctcgaggtc gacggtatcg ataagcttga tatcgaattc gcggccgcct ctctctctct     180
ctatctctat ctctcgattt gggggagttc cgtcacggtg gactagtacg tctcgttgcc     240
gttggtggcg tagtcggaat taatttcctc ggcgttgaga ttcacatggt ctagaattct     300
agctaagtgg ttgttgttgt tgttacgatt tccgatttct cgagtttttt tttttatatt     360
tagcttctgt ttcgtttatc cctcccggag acactccttg gtcgaatctc tcatgctgag     420
gtgttttgga cacttgttgt caagaagaaa ccagttttgg ttctgattaa tcgttggttg     480
gaaaatatac tcaattccag gccatgcctt cacttcaact attgcagtta actgagcggg     540 gtcgggtct tgtagcgtca agacgaaat ctatactgct tgcggctggg attgtagctg      600
ctggtggaac tgctgtttac ctgaaatcaa gggtcgcttc ccggaggcct gattcttcgc     660
gtctttgcaa tggtcagagt gatgatgatg agactttgga aaagctgact gcaactgatc     720
aaaatgcaaa gataaccacg aaaagaaga aaggaggagg attgaagtct cttcaggttc     780
tgactgctat tcttctctct cagatgggaa aaatgggtgc cagggatctt ttggcactag     840
tcgccaccgt ggttttcaga acagctttga gcaatagatt ggcaaaagtg caaggtttcc     900
ttttccgtgc tgctttctta aggcgtgcgc cactgtttct acggctcatc tccgagaata     960
ttatgttgtg tttcatgcta tcaacattgc actctacttc aaagtacata actggggcat    1020
tgagtttgcg attcagaaag atattgacca agattatcca ttcacactat tttgagaata    1080
```

```
tggtatatta caaaatatca cacgtggatg gtcggattac gcaccctgaa caaagaattg    1140
ccagcgatgt accaagattc tcctcagagt tgagcgatct tatactggat gatttgacgg    1200
cggttactga tggaattttg tatgcatggc gcctgtgttc atatgctagt ccaaaataca    1260
tcttctggat actggcctat gtactggggg ctgggacggc gataagaaac ttttctcctt    1320
cttttgggaa attgatgtcc aaggaacagc agttagaagg agagtaccgg caacttcatt    1380
cacgcttaag gactcattcg gaaagcatag cattctatgg tggggaaacc agggaagaat    1440
ctcatataca acaaaagttc aagaatcttg ttagccatat gagtcacgtg cttcatgatc    1500
actggtggtt tggtatgatc caagattttc tgctgaagta tcttgggggcc acagttgcag    1560 ttattctgat tatcgaacca ttcttctctg ggcatctaag acctgacgac tcgaccttag    1620
gaagagctga gatgcttagc aatataagat atcacactag tgtcattata tctctctttc    1680
aggcgttggg aacactttct ataagttcca ggcggctcaa ccgactcagt ggttatgctg    1740
accgaatcca tgagttgatg gctgtctcaa gagaactcag tggtgatgat aaatcgtctt    1800
tccagagaaa tagaagcaga aattatctaa gtgaagctaa ttatgtagag ttttccgatg    1860
tcaaggttgt tactccaacc ggaaatgttt tggtggagga tctcacccct cgagttgagc    1920
aagggtctaa tcttctgatt acaggtccta atggaagtgg caagagttcc cttttccgag    1980
tattaggagg tctatggccc ctggtgtctg gacatattgt gaagccagga gttggttctg    2040
atcttaacaa ggagatcttc tatgtgccgc aacggcctta tatggcagta ggaacacttc    2100
gtgaccagtt aatatatcct cttacttctg gccaagagag tgaactgctc actgagattg    2160
gaatggtgga gctattgaaa aatgttgatc tagaatattt attggatcgc taccaacctg    2220
aaaaagaggt taattggggt gatgaattat ctcttggaga gcaacagaga ttgggtatgg    2280
ccagactatt ctaccacaaa cccaaatttg caattctaga tgaatgcaca agtgctgtca    2340
caactgatat ggaagaacgc tttgccgcta aggttcgagc tatgggaact tcttgcataa    2400
caatctccca tcgtccagcg cttgttgcat tccatgatgt tgttctgtca ttagacggtg    2460
aaggaggatg gagtgttcat tacaagaggg atgactctgc ccttctgacg gatgctgaaa    2520
ttgattcagt gaaaagttca gatacagatc ggcaaaatga tgcgatggtt gttcaacgag    2580
cgtttgctgc agctagaaag gaatctgcta ctaattcaaa ggctcagtcg taccagacac    2640
agttaattgc aagatcacct gttgtagata aaagtgtagt gttgcctcgt tttcctcaac    2700
ctcaaacatc ccaaagggct ttaccatcaa gagtagctgc aatgttaaac gtgttgatac    2760
ccactatatt tgacaagcaa ggagctcaac tgcttgctgt tgcttgcctt gtcgtctcaa    2820
gaacgctgat ctctgaccga atagcctctt tgaatgggac cactgtgaag tatgtcttgg    2880
agcaagataa ggcagccttt gttcgtttga ttggtttgag tgttctccaa agtggtgcat    2940
cttctataat tgctccttca ctaaggcatt taacgcaaag gctagcgtta gggtggagga    3000
ttcgtttgac tcaacatctg ctaaggaact atttgagaaa taatgcgttt acaaggtttt    3060
tccacatgtc aggcaatagt attgatgcgg accagagact cactcgtgac ctggaaaagt    3120
taaccgctga cttgtctgga cttcttactg gaatggtaaa gccatcggtt gacattctct    3180
ggttcacctg gaggatgaag ttactgactg gtcagagggg agttgccata ctttacacat    3240
atatgttact tggtcttggt tttctgagac gtgttgctcc cgatttcggt gatctagccg    3300
gtgaagaaca gcagcttgaa gggaagtttc ggtttatgca cgagaggctg aacactcatg    3360
ctgaatctat tgcattcttt ggaggtggag ctcgagaaaa ggctatggtt gacaaaaaat    3420
tcagggccct actggatcat tctctcatgc tcttgaggaa gaaatggttg tatggcatac    3480
```

```
ttgatgattt tgtgacaaag caacttccca ataatgtgac gtggggattg agtttattgt    3540
atgccctaga acacaaggga gacagagcac ttgtctccac tcaaggtgaa ttggcacatg    3600
cattgcggta tctagcttct gttgtctccc aaagctttat ggcttttggc gatattcttg    3660
aactacacaa gaagttcctg gagctctctg gtggtattaa cagaattttt gagctcgatg    3720 agttttttgga tgcttctcag tcaggtgtta cctcagaaaa tcaaacaagt cgtttggatt    3780
ctcaagatct actttccttt tcggaggtgg atatcattac ccctgctcag aaattgatgg    3840
ctagcaagtt gtcgtgtgaa atagtttcag ggaaaagcct gctcgtcaca ggtccaaatg    3900
gtagtggaaa gacttcagta tttagagtcc ttagagatat ctggcccact gtatgtggaa    3960
gacttaccaa accatcattg gatatcaaag aacttgggtc agggaatggc atgttttttg    4020
tcccgcagcg accttataca tgtttaggga cactgagaga tcaaattata taccctctat    4080
ctaaagaaga agcagagaaa agggcagcaa agttgtacac cagtggagag agctcaacag    4140
aagctggaag cattctggat tctcatttga aaaccattct ggagaatgtt cggttagttt    4200
atctcttgga aagagactta ggtggttggg atgctactac caattgggaa gacatattat    4260
ctcttggaga gcaacagaga ttaggcatgg cacgtttatt ctttcacagg ccgaagtttg    4320
gagtccttga tgaatgcaca aatgcgacga gtgttgatgt tgaggaacag ctctatagag    4380
ttgcacgaga catgggagtc actttcataa cctcatcaca acggccggct ctgatcccat    4440
tccattcctt ggagctaagg ctgattgatg gagaaggaaa ctgggagctc cgttcgatcg    4500
aacagacaac agagtgaact cagcaaaaca tttttagaaa ggtctatata gttgttaaag    4560
aaaaaagtaa taaagttaaa gccattagac gatgcaagct atatggtatg tagtatatgg    4620
attcttcctc gatcgcaagg agtggaagag aatgcgtcga tgctagtgct tttgttagaa    4680
ttggaggatt tgatttgatt ctagatatat ataaatgtag gcgattgaat tggtggagca    4740
ttttgagttc tcctatggag tatggtctta gctttgaaca aacaaagaat atagtgatca    4800
ctcaaataat gtacagttcg tttcaatttc ctttgttggg attagttttt ctatcttata    4860
attaaaagaa tgaaattgaa gtgggcggcc gcgaattcct gcagcccggg ggatccacta    4920
gttctagagc ggccgccacc gcggtggagc tccagctttt gttcccttta gtgagggtta    4980
atttcgagct tggcgtaatc atggtcatag ctgtttcctg tgtgaaattg tatccgctca    5040
caattccaca caacatacga gccggaagca taa                                 5073
```

<210> SEQ ID NO 2
<211> LENGTH: 1336
<212> TYPE: PRT
<213> ORGANISM: Arabidopsis thaliana

<400> SEQUENCE: 2

```
Met Pro Ser Leu Gln Leu Leu Gln Leu Thr Glu Arg Gly Arg Gly Leu
1               5                   10                  15

Val Ala Ser Arg Arg Lys Ser Ile Leu Leu Ala Ala Gly Ile Val Ala
            20                  25                  30

Ala Gly Gly Thr Ala Val Tyr Leu Lys Ser Arg Val Ala Ser Arg Arg
        35                  40                  45

Pro Asp Ser Ser Arg Leu Cys Asn Gly Gln Ser Asp Asp Asp Glu Thr
    50                  55                  60

Leu Glu Lys Leu Thr Ala Thr Asp Gln Asn Ala Lys Ile Thr Thr Lys
65                  70                  75                  80

Lys Lys Lys Gly Gly Gly Leu Lys Ser Leu Gln Val Leu Thr Ala Ile
```

-continued

```
                 85                  90                  95
Leu Leu Ser Gln Met Gly Lys Met Gly Ala Arg Asp Leu Leu Ala Leu
                100                 105                 110
Val Ala Thr Val Val Phe Arg Thr Ala Leu Ser Asn Arg Leu Ala Lys
                115                 120                 125
Val Gln Gly Phe Leu Phe Arg Ala Ala Phe Leu Arg Arg Ala Pro Leu
            130                 135                 140
Phe Leu Arg Leu Ile Ser Glu Asn Ile Met Leu Cys Phe Met Leu Ser
145                 150                 155                 160
Thr Leu His Ser Thr Ser Lys Tyr Ile Thr Gly Ala Leu Ser Leu Arg
                165                 170                 175
Phe Arg Lys Ile Leu Thr Lys Ile Ile His Ser His Tyr Phe Glu Asn
                180                 185                 190
Met Val Tyr Tyr Lys Ile Ser His Val Asp Gly Arg Ile Thr His Pro
                195                 200                 205
Glu Gln Arg Ile Ala Ser Asp Val Pro Arg Phe Ser Ser Glu Leu Ser
            210                 215                 220
Asp Leu Ile Leu Asp Asp Leu Thr Ala Val Thr Asp Gly Ile Leu Tyr
225                 230                 235                 240
Ala Trp Arg Leu Cys Ser Tyr Ala Ser Pro Lys Tyr Ile Phe Trp Ile
                245                 250                 255
Leu Ala Tyr Val Leu Gly Ala Gly Thr Ala Ile Arg Asn Phe Ser Pro
                260                 265                 270
Ser Phe Gly Lys Leu Met Ser Lys Glu Gln Gln Leu Glu Gly Glu Tyr
                275                 280                 285
Arg Gln Leu His Ser Arg Leu Arg Thr His Ser Glu Ser Ile Ala Phe
            290                 295                 300
Tyr Gly Gly Glu Thr Arg Glu Glu Ser His Ile Gln Gln Lys Phe Lys
305                 310                 315                 320
Asn Leu Val Ser His Met Ser His Val Leu His Asp His Trp Trp Phe
                325                 330                 335
Gly Met Ile Gln Asp Phe Leu Leu Lys Tyr Leu Gly Ala Thr Val Ala
            340                 345                 350
Val Ile Leu Ile Ile Glu Pro Phe Phe Ser Gly His Leu Arg Pro Asp
            355                 360                 365
Asp Ser Thr Leu Gly Arg Ala Glu Met Leu Ser Asn Ile Arg Tyr His
            370                 375                 380
Thr Ser Val Ile Ile Ser Leu Phe Gln Ala Leu Gly Thr Leu Ser Ile
385                 390                 395                 400
Ser Ser Arg Arg Leu Asn Arg Leu Ser Gly Tyr Ala Asp Arg Ile His
                405                 410                 415
Glu Leu Met Ala Val Ser Arg Glu Leu Ser Gly Asp Asp Lys Ser Ser
            420                 425                 430
Phe Gln Arg Asn Arg Ser Arg Asn Tyr Leu Ser Glu Ala Asn Tyr Val
            435                 440                 445
Glu Phe Ser Asp Val Lys Val Val Thr Pro Thr Gly Asn Val Leu Val
            450                 455                 460
Glu Asp Leu Thr Leu Arg Val Glu Gln Gly Ser Asn Leu Leu Ile Thr
465                 470                 475                 480
Gly Pro Asn Gly Ser Gly Lys Ser Ser Leu Phe Arg Val Leu Gly Gly
                485                 490                 495
Leu Trp Pro Leu Val Ser Gly His Ile Val Lys Pro Gly Val Gly Ser
                500                 505                 510
```

-continued

```
Asp Leu Asn Lys Glu Ile Phe Tyr Val Pro Gln Arg Pro Tyr Met Ala
            515                 520                 525
Val Gly Thr Leu Arg Asp Gln Leu Ile Tyr Pro Leu Thr Ser Gly Gln
        530                 535                 540
Glu Ser Glu Leu Leu Thr Glu Ile Gly Met Val Glu Leu Leu Lys Asn
545                 550                 555                 560
Val Asp Leu Glu Tyr Leu Leu Asp Arg Tyr Gln Pro Glu Lys Glu Val
                565                 570                 575
Asn Trp Gly Asp Glu Leu Ser Leu Gly Glu Gln Gln Arg Leu Gly Met
            580                 585                 590
Ala Arg Leu Phe Tyr His Lys Pro Lys Phe Ala Ile Leu Asp Glu Cys
        595                 600                 605
Thr Ser Ala Val Thr Thr Asp Met Glu Glu Arg Phe Ala Ala Lys Val
        610                 615                 620
Arg Ala Met Gly Thr Ser Cys Ile Thr Ile Ser His Arg Pro Ala Leu
625                 630                 635                 640
Val Ala Phe His Asp Val Val Leu Ser Leu Asp Gly Glu Gly Gly Trp
                645                 650                 655
Ser Val His Tyr Lys Arg Asp Asp Ser Ala Leu Leu Thr Asp Ala Glu
            660                 665                 670
Ile Asp Ser Val Lys Ser Asp Thr Asp Arg Gln Asn Asp Ala Met
        675                 680                 685
Val Val Gln Arg Ala Phe Ala Ala Arg Lys Glu Ser Ala Thr Asn
        690                 695                 700
Ser Lys Ala Gln Ser Tyr Gln Thr Gln Leu Ile Ala Arg Ser Pro Val
705                 710                 715                 720
Val Asp Lys Ser Val Val Leu Pro Arg Phe Pro Gln Pro Gln Thr Ser
                725                 730                 735
Gln Arg Ala Leu Pro Ser Arg Val Ala Ala Met Leu Asn Val Leu Ile
            740                 745                 750
Pro Thr Ile Phe Asp Lys Gln Gly Ala Gln Leu Leu Ala Val Ala Cys
        755                 760                 765
Leu Val Val Ser Arg Thr Leu Ile Ser Asp Arg Ile Ala Ser Leu Asn
        770                 775                 780
Gly Thr Thr Val Lys Tyr Val Leu Glu Gln Asp Lys Ala Ala Phe Val
785                 790                 795                 800
Arg Leu Ile Gly Leu Ser Val Leu Gln Ser Gly Ala Ser Ser Ile Ile
                805                 810                 815
Ala Pro Ser Leu Arg His Leu Thr Gln Arg Leu Ala Leu Gly Trp Arg
            820                 825                 830
Ile Arg Leu Thr Gln His Leu Leu Arg Asn Tyr Leu Arg Asn Asn Ala
        835                 840                 845
Phe Tyr Lys Val Phe His Met Ser Gly Asn Ser Ile Asp Ala Asp Gln
        850                 855                 860
Arg Leu Thr Arg Asp Leu Glu Lys Leu Thr Ala Asp Leu Ser Gly Leu
865                 870                 875                 880
Leu Thr Gly Met Val Lys Pro Ser Val Asp Ile Leu Trp Phe Thr Trp
                885                 890                 895
Arg Met Lys Leu Leu Thr Gly Gln Arg Gly Val Ala Ile Leu Tyr Thr
            900                 905                 910
Tyr Met Leu Leu Gly Leu Gly Phe Leu Arg Arg Val Ala Pro Asp Phe
        915                 920                 925
```

-continued

```
Gly Asp Leu Ala Gly Glu Glu Gln Gln Leu Glu Gly Lys Phe Arg Phe
        930                 935                 940

Met His Glu Arg Leu Asn Thr His Ala Glu Ser Ile Ala Phe Phe Gly
945                 950                 955                 960

Gly Gly Ala Arg Glu Lys Ala Met Val Asp Lys Lys Phe Arg Ala Leu
                965                 970                 975

Leu Asp His Ser Leu Met Leu Leu Arg Lys Lys Trp Leu Tyr Gly Ile
            980                 985                 990

Leu Asp Asp Phe Val Thr Lys Gln Leu Pro Asn Asn Val Thr Trp Gly
        995                 1000                1005

Leu Ser Leu Leu Tyr Ala Leu Glu His Lys Gly Asp Arg Ala Leu
    1010            1015            1020

Val Ser Thr Gln Gly Glu Leu Ala His Ala Leu Arg Tyr Leu Ala
    1025            1030            1035

Ser Val Val Ser Gln Ser Phe Met Ala Phe Gly Asp Ile Leu Glu
    1040            1045            1050

Leu His Lys Lys Phe Leu Glu Leu Ser Gly Gly Ile Asn Arg Ile
    1055            1060            1065

Phe Glu Leu Asp Glu Phe Leu Asp Ala Ser Gln Ser Gly Val Thr
    1070            1075            1080

Ser Glu Asn Gln Thr Ser Arg Leu Asp Ser Gln Asp Leu Leu Ser
    1085            1090            1095

Phe Ser Glu Val Asp Ile Ile Thr Pro Ala Gln Lys Met Ala Ser
    1100            1105            1110

Lys Leu Ser Cys Glu Ile Val Ser Gly Lys Ser Leu Leu Val Thr
    1115            1120            1125

Gly Pro Asn Gly Ser Gly Lys Thr Ser Val Phe Arg Val Leu Arg
    1130            1135            1140

Asp Ile Trp Pro Thr Val Cys Gly Arg Leu Thr Lys Pro Ser Leu
    1145            1150            1155

Asp Ile Lys Glu Leu Gly Ser Gly Asn Gly Met Phe Phe Val Pro
    1160            1165            1170

Gln Arg Pro Tyr Thr Cys Leu Gly Thr Leu Arg Asp Gln Ile Ile
    1175            1180            1185

Tyr Pro Leu Ser Lys Glu Glu Ala Glu Lys Arg Ala Ala Lys Leu
    1190            1195            1200

Tyr Thr Ser Gly Glu Ser Ser Thr Glu Ala Gly Ser Ile Leu Asp
    1205            1210            1215

Ser His Leu Lys Thr Ile Leu Glu Asn Val Arg Leu Val Tyr Leu
    1220            1225            1230

Leu Glu Arg Asp Val Gly Gly Trp Asp Ala Thr Thr Asn Trp Glu
    1235            1240            1245

Asp Ile Leu Ser Leu Gly Glu Gln Gln Arg Leu Gly Met Ala Arg
    1250            1255            1260

Leu Phe Phe His Arg Pro Lys Phe Gly Val Leu Asp Glu Cys Thr
    1265            1270            1275

Asn Ala Thr Ser Val Asp Val Glu Glu Gln Leu Tyr Arg Val Ala
    1280            1285            1290

Arg Asp Met Gly Val Thr Phe Ile Thr Ser Ser Gln Arg Pro Ala
    1295            1300            1305

Leu Ile Pro Phe His Ser Leu Glu Leu Arg Leu Ile Asp Gly Glu
    1310            1315            1320

Gly Asn Trp Glu Leu Arg Ser Ile Glu Gln Thr Thr Glu
```

| 1325 | 1330 | 1335 |

<210> SEQ ID NO 3
<211> LENGTH: 29
<212> TYPE: DNA
<213> ORGANISM: Arabidopsis thaliana

<400> SEQUENCE: 3
ctctctctct atctctatct ctcgatttg                                  29

<210> SEQ ID NO 4
<211> LENGTH: 29
<212> TYPE: DNA
<213> ORGANISM: Arabidopsis thaliana

<400> SEQUENCE: 4
tctagctaag tggttgttgt tgttgttac                                  29

<210> SEQ ID NO 5
<211> LENGTH: 29
<212> TYPE: DNA
<213> ORGANISM: Arabidopsis thaliana

<400> SEQUENCE: 5
gccgttgaga ttcacatggt ctagaattc                                  29

<210> SEQ ID NO 6
<211> LENGTH: 29
<212> TYPE: DNA
<213> ORGANISM: Arabidopsis thaliana

<400> SEQUENCE: 6
atgaaacggt ggctagagtt acctgagta                                  29

<210> SEQ ID NO 7
<211> LENGTH: 29
<212> TYPE: DNA
<213> ORGANISM: Arabidopsis thaliana

<400> SEQUENCE: 7
tacactttta tctacaacag gtgatcttg                                  29

<210> SEQ ID NO 8
<211> LENGTH: 29
<212> TYPE: DNA
<213> ORGANISM: Arabidopsis thaliana

<400> SEQUENCE: 8
gcaattatag aagatgcacc actttggag                                  29

<210> SEQ ID NO 9
<211> LENGTH: 29
<212> TYPE: DNA
<213> ORGANISM: Arabidopsis thaliana

<400> SEQUENCE: 9
catagaatgc tatgctttcc gaatgagtc                                  29

<210> SEQ ID NO 10
<211> LENGTH: 29
<212> TYPE: DNA
<213> ORGANISM: Arabidopsis thaliana

<400> SEQUENCE: 10

```
cccaatgaga tctttagtgt ctctagcca                                    29

<210> SEQ ID NO 11
<211> LENGTH: 29
<212> TYPE: DNA
<213> ORGANISM: Arabidopsis thaliana

<400> SEQUENCE: 11
cccaatgaga tctttagtgt ctctagcca                                    29
```

The invention claimed is:

1. An isolated nucleic acid comprising a nucleotide sequence selected from the group consisting of:
   (i) the nucleotide sequence of SEQ ID NO:1;
   (ii) a nucleotide sequence encoding the amino acid sequence of SEQ ID NO:2;
   (iii) a nucleotide sequence which is at least 90% identical to the nucleotide sequence of SEQ ID NO:1; and
   (iv) a nucleotide sequence encoding a protein comprising an amino acid sequence that is at least 95% identical to the amino acid sequence of SEQ ID NO:2.

2. A vector comprising the nucleic acid of claim 1.

3. A transformed cell comprising the vector according to claim 2.

4. A nucleic acid construct comprising a promoter operable in a plant cell and a nucleotide sequence operatively associated with said promoter, wherein the nucleotide sequence is selected from the group consisting of:
   (i) the nucleotide sequence of SEQ ID NO:1;
   (ii) a nucleotide sequence encoding the amino acid sequence of SEQ ID NO:2;
   (iii) a nucleotide sequence encoding a protein comprising an amino acid sequence that is at least 95% identical to the amino acid sequence of SEQ ID NO:2; and
   (iv) a nucleotide sequence that differs from the nucleotide sequence of SEQ ID NO:1 due to the degeneracy of the genetic code.

5. A vector comprising the nucleic acid construct of claim 4.

6. A transformed cell comprising the nucleic acid construct of claim 4.

7. A transformed cell comprising the vector of claim 5.

8. A plant cell, a plant tissue, a plant, or a plant seed comprising the nucleic acid construct of claim 4.

9. A plant generated from a plant cell, a plant tissue, a plant or a plant seed comprising the nucleic acid construct of claim 4, wherein the plant comprises said construct.

10. A nucleic acid construct for antisense inhibition of an endogenous fatty acid transporter gene, wherein said construct comprises a promoter operable in a plant cell and said promoter is linked to a polynucleotide having at least 90% identity to the nucleotide sequence of SEQ ID NO:1 or a fragment thereof, wherein said polynucleotide is linked in antisense orientation relative to the promoter, and wherein said construct is effective for inhibition of expression of said endogenous gene.

11. A vector comprising the nucleic acid construct of claim 10.

12. A transformed cell comprising the nucleic acid construct of claim 10.

13. A transformed cell comprising the vector of claim 11.

14. A plant cell, a plant tissue, a plant, or a plant seed comprising the nucleic acid construct of claim 10.

15. A plant generated from a plant cell, a plant tissue, a plant or a plant seed comprising the nucleic acid construct of claim 14, wherein said plant comprises said construct.

16. A nucleic acid construct for RNAi inhibition of an endogenous fatty acid transporter gene, wherein said construct comprises a polynucleotide comprising a fragment of the nucleotide sequence of SEQ ID NO:1 and the complement of said fragment; wherein said polynucleotide is operably linked to a promoter operable in a plant cell; and wherein said construct is effective for inhibition of expression of said endogenous gene.

17. A vector comprising the nucleic acid construct of claim 16.

18. A transformed cell comprising the nucleic acid construct of claim 16.

19. A transformed cell comprising the vector of claim 17.

20. A plant cell, a plant tissue, a plant, or a plant seed comprising the nucleic acid of claim 16.

21. A plant generated from the plant cell, plant tissue, plant or plant seed of claim 20, wherein said plant comprises said construct.

22. A method of making a transformed plant cell having modulated fatty acid utilization, said method comprising transforming a plant cell with the nucleic acid construct of claim 4 to produce a transformed plant cell, said transformed plant cell having modulated fatty acid utilization compared to an untransformed plant cell.

23. The method of claim 22, further comprising generating a transgenic plant from said transformed plant cell.

24. A method of making a transformed plant cell having reduced fatty acid transporter gene expression, said method comprising transforming a plant cell of a type known to express said fatty acid transporter gene with the nucleic acid construct of claim 10 to produce a transformed plant cell, said transformed plant cell having reduced expression of said fatty acid transporter gene compared to an untransformed plant cell.

25. The method of claim 24, wherein the reduced fatty acid transporter gene expression results in increased oil content in the transformed plant cell.

26. The method of claim 24, further comprising generating a transgenic plant from said transformed plant cell.

27. A method of making a transformed plant cell having reduced fatty acid transporter gene expression, said method comprising transforming a plant cell of a type known to express said fatty acid transporter gene with the nucleic acid construct of claim 16 to produce a transformed plant cell, said transformed plant cell having reduced expression of said fatty acid transporter gene compared to an untransformed plant cell.

28. The method of claim 27, wherein the reduced fatty acid transporter gene expression results in increased oil content in the transformed plant cell.

29. The method of claim 27, further comprising regenerating a transgenic plant from said transformed plant cell.

30. A method of modulating fatty acid utilization in a plant cell comprising transforming a plant cell with the nucleic acid construct of claim 4, whereby expression of the nucleotide sequence of said nucleic acid construct results in modulation of fatty acid utilization in the plant cell.

31. A method for reducing expression of a fatty acid transporter gene in a plant cell, said method comprising: transforming a plant cell with the nucleic acid construct of claim 10, wherein transcription of the nucleotide sequence or fragment thereof of said nucleic acid construct reduces expression of said fatty acid transporter gene.

32. A method for reducing expression of a fatty acid transporter gene in an plant cell, said method comprising transforming a plant cell with the nucleic acid construct of claim 16, wherein transcription of the nucleotide sequence fragment or complement thereof of said nucleic acid construct reduces expression of said fatty acid transporter gene.

* * * * *

UNITED STATES PATENT AND TRADEMARK OFFICE
CERTIFICATE OF CORRECTION

PATENT NO. : 7,626,079 B2
APPLICATION NO. : 10/486376
DATED : December 1, 2009
INVENTOR(S) : Baker et al.

It is certified that error appears in the above-identified patent and that said Letters Patent is hereby corrected as shown below:

Columns 21 - 36: Please replace the Sequence Listing with the following:

```
                        SEQUENCE LISTING

<110>   Baker, Alison
            Slocombe, Stephen
            Graham, Ian

<120>   REGULATION OF PEROXISOMAL FATTY ACID TRANSPORT IN PLANTS

<130>   9052-183

<140>   US 10/486,376
    <141>   2004-01-20

<150>   PCT/GB02/03334
    <151>   2002-07-19

<150>   GB 0207883.0
    <151>   2002-04-05

<150>   GB 0117727.8
    <151>   2001-07-20

<160>   21

<170>   PatentIn version 3.3

<210>   1
    <211>   5073
    <212>   DNA
    <213>   Arabidopsis thaliana

<400>   1
    atgtgctgca aggcgattaa gttgggtaac gccagggttt tcccagtcac gacgttgtaa      60
aacgacggcc agtgaattgt aatacgactc actatagggc gaattgggta ccggccgcc      120 cctcgaggtc gacggtatcg ataagcttga tatcgaattc gcggccgcct ctctctctct     180
```

| | | | | | |
|---|---|---|---|---|---|
| ctatctctat | ctctcgattt | gggggagttc | cgtcacggtg | gactagtacg | tctcgttgcc | 240 |
| gttggtggcg | tagtcggaat | taatttcctc | ggcgttgaga | ttcacatggt | ctagaattct | 300 |
| agctaagtgg | ttgttgttgt | tgttacgatt | tccgatttct | cgagtttttt | tttttatatt | 360 |
| tagcttctgt | ttcgtttatc | cctcccggag | acactccttg | gtcgaatctc | tcatgctgag | 420 |
| gtgttttgga | cacttgttgt | caagaagaaa | ccagttttgg | ttctgattaa | tcgttggttg | 480 |
| gaaaatatac | tcaattccag | gccatgcctt | cacttcaact | attgcagtta | actgagcggg | 540 |
| gtcgggtct | tgtagcgtca | agacggaaat | ctatactgct | tgcggctggg | attgtagctg | 600 |
| ctggtggaac | tgctgtttac | ctgaaatcaa | gggtcgcttc | ccggaggcct | gattcttcgc | 660 |
| gtctttgcaa | tggtcagagt | gatgatgatg | agactttgga | aaagctgact | gcaactgatc | 720 |
| aaaatgcaaa | gataaccacg | aaaaagaaga | aggaggagg | attgaagtct | cttcaggttc | 780 |
| tgactgctat | tcttctctct | cagatgggaa | aaatgggtgc | cagggatctt | ttggcactag | 840 |
| tcgccaccgt | ggttttcaga | acagctttga | gcaatagatt | ggcaaaagtg | caaggtttcc | 900 |
| ttttccgtgc | tgctttctta | aggcgtgcgc | cactgtttct | acggctcatc | tccgagaata | 960 |
| ttatgttgtg | tttcatgcta | tcaacattgc | actctacttc | aaagtacata | actggggcat | 1020 |
| tgagtttgcg | attcagaaag | atattgacca | agattatcca | ttcacactat | tttgagaata | 1080 |
| tggtatatta | caaaatatca | cacgtggatg | gtcggattac | gcaccctgaa | caaagaattg | 1140 |
| ccagcgatgt | accaagattc | tcctcagagt | tgagcgatct | tatactggat | gatttgacgg | 1200 |
| cggttactga | tggaattttg | tatgcatggc | gcctgtgttc | atatgctagt | ccaaaataca | 1260 |
| tcttctggat | actggcctat | gtactggggg | ctgggacggc | gataagaaac | ttttctcctt | 1320 |
| cttttgggaa | attgatgtcc | aaggaacagc | agttagaagg | agagtaccgg | caacttcatt | 1380 |
| cacgcttaag | gactcattcg | gaaagcatag | cattctatgg | tggggaaacc | agggaagaat | 1440 |
| ctcatataca | acaaaagttc | aagaatcttg | ttagccatat | gagtcacgtg | cttcatgatc | 1500 |
| actggtggtt | tggtatgatc | caagattttc | tgctgaagta | tcttggggcc | acagttgcag | 1560 |

```
ttattctgat tatcgaacca ttcttctctg ggcatctaag acctgacgac tcgaccttag   1620
gaagagctga gatgcttagc aatataagat atcacactag tgtcattata tctctctttc   1680
aggcgttggg aacactttct ataagttcca ggcggctcaa ccgactcagt ggttatgctg   1740
accgaatcca tgagttgatg gctgtctcaa gagaactcag tggtgatgat aaatcgtctt   1800
tccagagaaa tagaagcaga aattatctaa gtgaagctaa ttatgtagag ttttccgatg   1860
tcaaggttgt tactccaacc ggaaatgttt tggtggagga tctcaccctt cgagttgagc   1920
aagggtctaa tcttctgatt acaggtccta atggaagtgg caagagttcc cttttccgag   1980
tattaggagg tctatggccc ctggtgtctg gacatattgt gaagccagga gttggttctg   2040
atcttaacaa ggagatcttc tatgtgccgc aacggcctta tatggcagta ggaacacttc   2100
gtgaccagtt aatatatcct cttacttctg gccaagagag tgaactgctc actgagattg   2160
gaatggtgga gctattgaaa aatgttgatc tagaatattt attggatcgc taccaacctg   2220
aaaaagaggt taattggggt gatgaattat ctcttggaga gcaacagaga ttgggtatgg   2280
ccagactatt ctaccacaaa cccaaatttg caattctaga tgaatgcaca agtgctgtca   2340
caactgatat ggaagaacgc tttgccgcta aggttcgagc tatgggaact tcttgcataa   2400
caatctccca tcgtccagcg cttgttgcat tccatgatgt tgttctgtca ttagacggtg   2460
aaggaggatg gagtgttcat tacaagaggg atgactctgc ccttctgacg gatgctgaaa   2520
ttgattcagt gaaaagttca gatacagatc ggcaaaatga tgcgatggtt gttcaacgag   2580
cgtttgctgc agctagaaag gaatctgcta ctaattcaaa ggctcagtcg taccagacac   2640
agttaattgc aagatcacct gttgtagata aagtgtagt gttgcctcgt tttcctcaac   2700
ctcaaacatc ccaaagggct ttaccatcaa gagtagctgc aatgttaaac gtgttgatac   2760
ccactatatt tgacaagcaa ggagctcaac tgcttgctgt tgcttgcctt gtcgtctcaa   2820
gaacgctgat ctctgaccga atagcctctt tgaatgggac cactgtgaag tatgtcttgg   2880
agcaagataa ggcagccttt gttcgtttga ttggtttgag tgttctccaa agtggtgcat   2940
```

```
cttctataat tgctccttca ctaaggcatt taacgcaaag gctagcgtta gggtggagga    3000
ttcgtttgac tcaacatctg ctaaggaact atttgagaaa taatgcgttt tacaaggttt    3060
tccacatgtc aggcaatagt attgatgcgg accagagact cactcgtgac ctggaaaagt    3120
taaccgctga cttgtctgga cttcttactg gaatggtaaa gccatcggtt gacattctct    3180
ggttcacctg gaggatgaag ttactgactg gtcagagggg agttgccata ctttacacat    3240
atatgttact tggtcttggt tttctgagac gtgttgctcc cgatttcggt gatctagccg    3300
gtgaagaaca gcagcttgaa gggaagtttc ggtttatgca cgagaggctg aacactcatg    3360
ctgaatctat tgcattcttt ggaggtggag ctcgagaaaa ggctatggtt gacaaaaaat    3420
tcagggccct actggatcat tctctcatgc tcttgaggaa gaaatggttg tatggcatac    3480
ttgatgattt tgtgacaaag caacttccca ataatgtgac gtggggattg agtttattgt    3540
atgccctaga acacaaggga gacagagcac ttgtctccac tcaaggtgaa ttggcacatg    3600
cattgcggta tctagcttct gttgtctccc aaagctttat ggcttttggc gatattcttg    3660
aactacacaa gaagttcctg gagctctctg gtggtattaa cagaattttt gagctcgatg    3720
agtttttgga tgcttctcag tcaggtgtta cctcagaaaa tcaaacaagt cgtttggatt    3780
ctcaagatct actttccttt tcggaggtgg atatcattac ccctgctcag aaattgatgg    3840
ctagcaagtt gtcgtgtgaa atagtttcag ggaaaagcct gctcgtcaca ggtccaaatg    3900
gtagtggaaa gacttcagta tttagagtcc ttagagatat ctggcccact gtatgtggaa    3960
gacttaccaa accatcattg gatatcaaag aacttgggtc agggaatggc atgttttttg    4020
tcccgcagcg accttataca tgtttaggga cactgagaga tcaaattata taccctctat    4080
ctaaagaaga agcagagaaa agggcagcaa agttgtacac cagtggagag agctcaacag    4140
aagctggaag cattctggat tctcatttga aaccattct ggagaatgtt cggttagttt    4200
atctcttgga aagagacgta ggtggttggg atgctactac caattgggaa gacatattat    4260
ctcttggaga gcaacagaga ttaggcatgg cacgtttatt ctttcacagg ccgaagtttg    4320
```

```
gagtccttga tgaatgcaca aatgcgacga gtgttgatgt tgaggaacag ctctatagag    4380
ttgcacgaga catgggagtc actttcataa cctcatcaca acggccggct ctgatcccat    4440
tccattcctt ggagctaagg ctgattgatg gagaaggaaa ctgggagctc cgttcgatcg    4500
aacagacaac agagtgaact cagcaaaaca ttttagaaa  ggtctatata gttgttaaag    4560
aaaaaagtaa taaagttaaa gccattagac gatgcaagct atatggtatg tagtatatgg    4620
attcttcctc gatcgcaagg agtggaagag aatgcgtcga tgctagtgct tttgttagaa    4680
ttggaggatt tgatttgatt ctagatatat ataaatgtag gcgattgaat tggtggagca    4740
ttttgagttc tcctatggag tatggtctta gctttgaaca aacaaagaat atagtgatca    4800
ctcaaataat gtacagttcg tttcaatttc ctttgttggg attagttttt ctatcttata    4860
attaaaagaa tgaaattgaa gtgggcggcc gcgaattcct gcagcccggg ggatccacta    4920
gttctagagc ggccgccacc gcggtggagc tccagctttt gttcccttta gtgagggtta    4980 attcgagct  tggcgtaatc atggtcatag ctgtttcctg tgtgaaattg tatccgctca    5040
caattccaca caacatacga gccggaagca taa                                 5073
```

<210> 2
<211> 1336
<212> PRT
<213> Arabidopsis thaliana

<400> 2

| Met | Pro | Ser | Leu | Gln | Leu | Leu | Gln | Leu | Thr | Glu | Arg | Gly | Arg | Gly | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Val | Ala | Ser | Arg | Arg | Lys | Ser | Ile | Leu | Leu | Ala | Ala | Gly | Ile | Val | Ala |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ala | Gly | Gly | Thr | Ala | Val | Tyr | Leu | Lys | Ser | Arg | Val | Ala | Ser | Arg | Arg |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

```
Pro Asp Ser Ser Arg Leu Cys Asn Gly Gln Ser Asp Asp Glu Thr
    50              55                  60

Leu Glu Lys Leu Thr Ala Thr Asp Gln Asn Ala Lys Ile Thr Thr Lys
65              70                  75                  80

Lys Lys Lys Gly Gly Gly Leu Lys Ser Leu Gln Val Leu Thr Ala Ile
            85              90                  95

Leu Leu Ser Gln Met Gly Lys Met Gly Ala Arg Asp Leu Leu Ala Leu
            100             105                 110

Val Ala Thr Val Val Phe Arg Thr Ala Leu Ser Asn Arg Leu Ala Lys
        115             120                 125

Val Gln Gly Phe Leu Phe Arg Ala Ala Phe Leu Arg Arg Ala Pro Leu
    130             135                 140

Phe Leu Arg Leu Ile Ser Glu Asn Ile Met Leu Cys Phe Met Leu Ser
145             150                 155                 160

Thr Leu His Ser Thr Ser Lys Tyr Ile Thr Gly Ala Leu Ser Leu Arg
            165             170                 175

Phe Arg Lys Ile Leu Thr Lys Ile Ile His Ser His Tyr Phe Glu Asn
            180             185                 190

Met Val Tyr Tyr Lys Ile Ser His Val Asp Gly Arg Ile Thr His Pro
        195             200                 205

Glu Gln Arg Ile Ala Ser Asp Val Pro Arg Phe Ser Ser Glu Leu Ser
    210             215                 220

Asp Leu Ile Leu Asp Asp Leu Thr Ala Val Thr Asp Gly Ile Leu Tyr
225             230                 235                 240
```

```
Ala Trp Arg Leu Cys Ser Tyr Ala Ser Pro Lys Tyr Ile Phe Trp Ile
            245                 250                 255

Leu Ala Tyr Val Leu Gly Ala Gly Thr Ala Ile Arg Asn Phe Ser Pro
            260                 265                 270

Ser Phe Gly Lys Leu Met Ser Lys Glu Gln Gln Leu Glu Gly Glu Tyr
            275                 280                 285

Arg Gln Leu His Ser Arg Leu Arg Thr His Ser Glu Ser Ile Ala Phe
        290                 295                 300

Tyr Gly Gly Glu Thr Arg Glu Glu Ser His Ile Gln Gln Lys Phe Lys
305                 310                 315                 320

Asn Leu Val Ser His Met Ser His Val Leu His Asp His Trp Trp Phe
                325                 330                 335

Gly Met Ile Gln Asp Phe Leu Leu Lys Tyr Leu Gly Ala Thr Val Ala
            340                 345                 350

Val Ile Leu Ile Ile Glu Pro Phe Phe Ser Gly His Leu Arg Pro Asp
        355                 360                 365

Asp Ser Thr Leu Gly Arg Ala Glu Met Leu Ser Asn Ile Arg Tyr His
    370                 375                 380

Thr Ser Val Ile Ile Ser Leu Phe Gln Ala Leu Gly Thr Leu Ser Ile
385                 390                 395                 400

Ser Ser Arg Arg Leu Asn Arg Leu Ser Gly Tyr Ala Asp Arg Ile His
            405                 410                 415

Glu Leu Met Ala Val Ser Arg Glu Leu Ser Gly Asp Asp Lys Ser Ser
            420                 425                 430
```

CERTIFICATE OF CORRECTION (continued)
U.S. Pat. No. 7,626,079 B2

```
Phe Gln Arg Asn Arg Ser Arg Asn Tyr Leu Ser Glu Ala Asn Tyr Val
        435                 440                 445

Glu Phe Ser Asp Val Lys Val Val Thr Pro Thr Gly Asn Val Leu Val
    450                 455                 460

Glu Asp Leu Thr Leu Arg Val Glu Gln Gly Ser Asn Leu Leu Ile Thr
465                 470                 475                 480

Gly Pro Asn Gly Ser Gly Lys Ser Ser Leu Phe Arg Val Leu Gly Gly
                485                 490                 495

Leu Trp Pro Leu Val Ser Gly His Ile Val Lys Pro Gly Val Gly Ser
            500                 505                 510

Asp Leu Asn Lys Glu Ile Phe Tyr Val Pro Gln Arg Pro Tyr Met Ala
        515                 520                 525

Val Gly Thr Leu Arg Asp Gln Leu Ile Tyr Pro Leu Thr Ser Gly Gln
    530                 535                 540

Glu Ser Glu Leu Leu Thr Glu Ile Gly Met Val Glu Leu Leu Lys Asn
545                 550                 555                 560

Val Asp Leu Glu Tyr Leu Leu Asp Arg Tyr Gln Pro Glu Lys Glu Val
            565                 570                 575

Asn Trp Gly Asp Glu Leu Ser Leu Gly Glu Gln Gln Arg Leu Gly Met
            580                 585                 590

Ala Arg Leu Phe Tyr His Lys Pro Lys Phe Ala Ile Leu Asp Glu Cys
        595                 600                 605

Thr Ser Ala Val Thr Thr Asp Met Glu Glu Arg Phe Ala Ala Lys Val
610                 615                 620
```

```
Arg Ala Met Gly Thr Ser Cys Ile Thr Ile Ser His Arg Pro Ala Leu
625                 630                 635                 640

Val Ala Phe His Asp Val Val Leu Ser Leu Asp Gly Glu Gly Gly Trp
                645                 650                 655

Ser Val His Tyr Lys Arg Asp Asp Ser Ala Leu Leu Thr Asp Ala Glu
            660                 665                 670

Ile Asp Ser Val Lys Ser Ser Asp Thr Asp Arg Gln Asn Asp Ala Met
            675                 680                 685

Val Val Gln Arg Ala Phe Ala Ala Arg Lys Glu Ser Ala Thr Asn
    690                 695                 700

Ser Lys Ala Gln Ser Tyr Gln Thr Gln Leu Ile Ala Arg Ser Pro Val
705                 710                 715                 720

Val Asp Lys Ser Val Val Leu Pro Arg Phe Pro Gln Pro Gln Thr Ser
            725                 730                 735

Gln Arg Ala Leu Pro Ser Arg Val Ala Ala Met Leu Asn Val Leu Ile
                740                 745                 750

Pro Thr Ile Phe Asp Lys Gln Gly Ala Gln Leu Leu Ala Val Ala Cys
            755                 760                 765

Leu Val Val Ser Arg Thr Leu Ile Ser Asp Arg Ile Ala Ser Leu Asn
    770                 775                 780

Gly Thr Thr Val Lys Tyr Val Leu Glu Gln Asp Lys Ala Ala Phe Val
785                 790                 795                 800

Arg Leu Ile Gly Leu Ser Val Leu Gln Ser Gly Ala Ser Ser Ile Ile
                805                 810                 815
```

```
Ala Pro Ser Leu Arg His Leu Thr Gln Arg Leu Ala Leu Gly Trp Arg
            820                 825                 830

Ile Arg Leu Thr Gln His Leu Leu Arg Asn Tyr Leu Arg Asn Asn Ala
            835                 840                 845

Phe Tyr Lys Val Phe His Met Ser Gly Asn Ser Ile Asp Ala Asp Gln
            850                 855                 860

Arg Leu Thr Arg Asp Leu Glu Lys Leu Thr Ala Asp Leu Ser Gly Leu
865                 870                 875                 880

Leu Thr Gly Met Val Lys Pro Ser Val Asp Ile Leu Trp Phe Thr Trp
                885                 890                 895

Arg Met Lys Leu Leu Thr Gly Gln Arg Gly Val Ala Ile Leu Tyr Thr
                900                 905                 910

Tyr Met Leu Leu Gly Leu Gly Phe Leu Arg Arg Val Ala Pro Asp Phe
            915                 920                 925

Gly Asp Leu Ala Gly Glu Glu Gln Gln Leu Glu Gly Lys Phe Arg Phe
        930                 935                 940

Met His Glu Arg Leu Asn Thr His Ala Glu Ser Ile Ala Phe Phe Gly
945                 950                 955                 960

Gly Gly Ala Arg Glu Lys Ala Met Val Asp Lys Lys Phe Arg Ala Leu
                965                 970                 975

Leu Asp His Ser Leu Met Leu Leu Arg Lys Lys Trp Leu Tyr Gly Ile
            980                 985                 990

Leu Asp Asp Phe Val Thr Lys Gln  Leu Pro Asn Asn Val  Thr Trp Gly
            995                 1000                 1005
```

```
Leu Ser Leu Leu Tyr Ala Leu Glu His Lys Gly Asp Arg Ala Leu
        1010            1015            1020

Val Ser Thr Gln Gly Glu Leu Ala His Ala Leu Arg Tyr Leu Ala
        1025            1030            1035

Ser Val Val Ser Gln Ser Phe Met Ala Phe Gly Asp Ile Leu Glu
        1040            1045            1050

Leu His Lys Lys Phe Leu Glu Leu Ser Gly Gly Ile Asn Arg Ile
        1055            1060            1065

Phe Glu Leu Asp Glu Phe Leu Asp Ala Ser Gln Ser Gly Val Thr
        1070            1075            1080

Ser Glu Asn Gln Thr Ser Arg Leu Asp Ser Gln Asp Leu Leu Ser
        1085            1090            1095

Phe Ser Glu Val Asp Ile Ile Thr Pro Ala Gln Lys Met Ala Ser
        1100            1105            1110

Lys Leu Ser Cys Glu Ile Val Ser Gly Lys Ser Leu Leu Val Thr
        1115            1120            1125

Gly Pro Asn Gly Ser Gly Lys Thr Ser Val Phe Arg Val Leu Arg
        1130            1135            1140

Asp Ile Trp Pro Thr Val Cys Gly Arg Leu Thr Lys Pro Ser Leu
        1145            1150            1155

Asp Ile Lys Glu Leu Gly Ser Gly Asn Gly Met Phe Phe Val Pro
        1160            1165            1170

Gln Arg Pro Tyr Thr Cys Leu Gly Thr Leu Arg Asp Gln Ile Ile
        1175            1180            1185
```

Tyr Pro Leu Ser Lys Glu Glu Ala Glu Lys Arg Ala Ala Lys Leu
    1190            1195                1200

Tyr Thr Ser Gly Glu Ser Ser Thr Glu Ala Gly Ser Ile Leu Asp
    1205            1210                1215

Ser His Leu Lys Thr Ile Leu Glu Asn Val Arg Leu Val Tyr Leu
    1220            1225                1230

Leu Glu Arg Asp Val Gly Gly Trp Asp Ala Thr Thr Asn Trp Glu
    1235            1240                1245

Asp Ile Leu Ser Leu Gly Glu Gln Gln Arg Leu Gly Met Ala Arg
    1250            1255                1260

Leu Phe Phe His Arg Pro Lys Phe Gly Val Leu Asp Glu Cys Thr
    1265            1270                1275

Asn Ala Thr Ser Val Asp Val Glu Glu Gln Leu Tyr Arg Val Ala
    1280            1285                1290

Arg Asp Met Gly Val Thr Phe Ile Thr Ser Ser Gln Arg Pro Ala
    1295            1300                1305

Leu Ile Pro Phe His Ser Leu Glu Leu Arg Leu Ile Asp Gly Glu
    1310            1315                1320

Gly Asn Trp Glu Leu Arg Ser Ile Glu Gln Thr Thr Glu
    1325            1330                1335

<210> 3
<211> 29
<212> DNA
<213> Arabidopsis thaliana

```
<400>  3
ctctctctct atctctatct ctcgatttg                              29

<210>  4
<211>  29
<212>  DNA
<213>  Arabidopsis thaliana

<400>  4
tctagctaag tggttgttgt tgttgttac                              29

<210>  5
<211>  29
<212>  DNA
<213>  Arabidopsis thaliana

<400>  5
gccgttgaga ttcacatggt ctagaattc                              29

<210>  6
<211>  29
<212>  DNA
<213>  Arabidopsis thaliana

<400>  6
atgaaacggt ggctagagtt acctgagta                              29

<210>  7
<211>  29
<212>  DNA
<213>  Arabidopsis thaliana

<400>  7
tacacttta tctacaacag gtgatcttg                               29

<210>  8
<211>  29
<212>  DNA
<213>  Arabidopsis thaliana
```

```
<400>  8
gcaattatag aagatgcacc actttggag                                29

<210>  9
<211>  29
<212>  DNA
<213>  Arabidopsis thaliana

<400>  9
catagaatgc tatgctttcc gaatgagtc                                29

<210>  10
<211>  29
<212>  DNA
<213>  Arabidopsis thaliana

<400>  10
cccaatgaga tctttagtgt ctctagcca                                29

<210>  11
<211>  29
<212>  DNA
<213>  Arabidopsis thaliana

<400>  11
cccaatgaga tctttagtgt ctctagcca                                29

<210>  12
<211>  8
<212>  PRT
<213>  Artificial

<220>
<223>  Human and yeast peroxisomal ABC transporter sequence

<400>  12

Asn Ser Glu Glu Ile Ala Phe Tyr
 1               5
```

```
<210>  13
<211>  7
<212>  PRT
<213>  Artificial

<220>
<223>  CTS sequence

<220>
<221>  MISC_FEATURE
<222>  (2)..(2)
<223>  Xaa can be Ser or Ala

<220>
<221>  MISC_FEATURE
<222>  (7)..(7)
<223>  Xaa can be Tyr or Phe

<400>  13

His Xaa Ser Ile Ala Phe Xaa
1               5

<210>  14
<211>  14
<212>  PRT
<213>  Artificial

<220>
<223>  Animal peroxisomal ABC transporter sequence

<400>  14

Pro Gln Arg Pro Tyr Met Thr Leu Gly Thr Leu Arg Asp Gln
1               5                   10

<210>  15
<211>  14
<212>  PRT
<213>  Artificial

<220>
<223>  CTS sequence
```

```
<220>
<221>  MISC_FEATURE
<222>  (6)..(6)
<223>  Xaa may be Met or Thr

<220>
<221>  MISC_FEATURE
<222>  (7)..(7)
<223>  Xaa may be Ala or Cys

<400>  15
```

Pro Gln Arg Pro Tyr Xaa Xaa Leu Gly Thr Leu Arg Asp Gln
1               5                   10

```
<210>  16
<211>  745
<212>  PRT
<213>  Homo sapiens

<400>  16
```

Met Pro Val Leu Ser Arg Pro Arg Pro Trp Arg Gly Asn Thr Leu Lys
1               5                   10                  15

Arg Thr Ala Val Leu Leu Ala Leu Ala Ala Tyr Gly Ala His Lys Val
            20                  25                  30

Tyr Pro Leu Val Arg Gln Cys Leu Ala Pro Ala Arg Gly Leu Gln Ala
        35                  40                  45

Pro Ala Gly Glu Pro Thr Gln Glu Ala Ser Gly Val Ala Ala Ala Lys
    50                  55                  60

Ala Gly Met Asn Arg Val Phe Leu Gln Arg Leu Leu Trp Leu Leu Arg
65                  70                  75                  80

Leu Leu Phe Pro Arg Val Leu Cys Arg Glu Thr Gly Leu Leu Ala Leu
                85                  90                  95

```
His Ser Ala Ala Leu Val Ser Arg Thr Phe Leu Ser Val Tyr Val Ala
            100                 105                 110

Arg Leu Asp Gly Arg Leu Ala Arg Cys Ile Ala Arg Lys Asp Pro Arg
        115                 120                 125

Ala Phe Gly Trp Gln Leu Leu Gln Trp Leu Leu Ile Ala Leu Pro Ala
    130                 135                 140

Thr Phe Val Asn Ser Ala Ile Arg Tyr Leu Glu Gly Gln Leu Ala Leu
145                 150                 155                 160

Ser Phe Arg Ser Arg Leu Val Ala His Ala Tyr Arg Leu Tyr Phe Ser
                165                 170                 175

Gln Gln Thr Tyr Tyr Arg Val Ser Asn Met Asp Gly Arg Leu Arg Asn
            180                 185                 190

Pro Asp Gln Ser Leu Thr Glu Asp Val Val Ala Phe Ala Ala Ser Val
        195                 200                 205

Ala His Leu Tyr Ser Asn Leu Thr Lys Pro Leu Leu Asp Val Ala Val
    210                 215                 220

Thr Ser Tyr Thr Leu Leu Arg Ala Ala Arg Ser Arg Gly Ala Gly Thr
225                 230                 235                 240

Ala Trp Pro Ser Ala Ile Ala Gly Leu Val Val Phe Leu Thr Ala Asn
                245                 250                 255

Val Leu Arg Ala Phe Ser Pro Lys Phe Gly Glu Leu Val Ala Glu Glu
            260                 265                 270

Ala Arg Arg Lys Gly Glu Leu Arg Tyr Met His Ser Arg Val Val Ala
            275                 280                 285
```

Asn Ser Glu Glu Ile Ala Phe Tyr Gly Gly His Glu Val Glu Leu Ala
    290             295             300

Leu Leu Gln Arg Ser Tyr Gln Asp Leu Ala Ser Gln Ile Asn Leu Ile
305             310             315                 320

Leu Leu Glu Arg Leu Trp Tyr Val Met Leu Glu Gln Phe Leu Met Lys
            325             330             335

Tyr Val Trp Ser Ala Ser Gly Leu Leu Met Val Ala Val Pro Ile Ile
            340             345             350

Thr Ala Thr Gly Tyr Ser Glu Ser Asp Ala Glu Ala Val Lys Lys Ala
            355             360             365

Ala Leu Glu Lys Lys Glu Glu Leu Val Ser Glu Arg Thr Glu Ala
    370             375             380

Phe Thr Ile Ala Arg Asn Leu Leu Thr Ala Ala Ala Asp Ala Ile Glu
385             390             395                 400

Arg Ile Met Ser Ser Tyr Lys Glu Val Thr Glu Leu Ala Gly Tyr Thr
                405             410             415

Ala Arg Val His Glu Met Phe Gln Val Phe Glu Asp Val Gln Arg Cys
            420             425             430

His Phe Lys Arg Pro Arg Glu Leu Glu Asp Ala Gln Ala Gly Ser Gly
            435             440             445

Thr Ile Gly Arg Ser Gly Val Arg Val Glu Gly Pro Leu Lys Ile Arg
            450             455             460

Gly Gln Val Val Asp Val Glu Gln Gly Ile Ile Cys Glu Asn Ile Pro
465             470             475                 480

Ile Val Thr Pro Ser Gly Glu Val Val Ala Ser Leu Asn Ile Arg
                485             490             495

Val Glu Glu Gly Met His Leu Leu Ile Thr Gly Pro Asn Gly Cys Gly
                500             505             510

Lys Ser Ser Leu Phe Arg Ile Leu Gly Gly Leu Trp Pro Thr Tyr Gly
        515             520             525

Gly Val Leu Tyr Lys Pro Pro Gln Arg Met Phe Tyr Ile Pro Gln
    530             535             540

Arg Pro Tyr Met Ser Val Gly Ser Leu Arg Asp Gln Val Ile Tyr Pro
545             550             555             560

Asp Ser Val Glu Asp Met Gln Arg Lys Gly Tyr Ser Glu Gln Asp Leu
                565             570             575

Glu Ala Ile Leu Asp Val Val His Leu His His Ile Leu Gln Arg Glu
            580             585             590

Gly Gly Trp Glu Ala Met Cys Asp Trp Lys Asp Val Leu Ser Gly Gly
        595             600             605

Glu Lys Gln Arg Ile Gly Met Ala Arg Met Phe Tyr His Arg Pro Lys
    610             615             620

Tyr Ala Leu Leu Asp Glu Cys Thr Ser Ala Val Ser Ile Asp Val Glu
625             630             635             640

Gly Lys Ile Phe Gln Ala Ala Lys Asp Ala Gly Ile Ala Leu Leu Ser
            645             650             655

Ile Thr His Arg Pro Ser Leu Trp Lys Tyr His Thr His Leu Leu Gln
        660             665             670

```
Phe Asp Gly Glu Gly Gly Trp Lys Phe Glu Lys Leu Asp Ser Ala Ala
        675                 680                 685

Arg Leu Ser Leu Thr Glu Glu Lys Gln Arg Leu Glu Gln Gln Leu Ala
        690                 695                 700

Gly Ile Pro Lys Met Gln Arg Arg Leu Gln Glu Leu Cys Gln Ile Leu
705                 710                 715                 720

Gly Glu Ala Val Ala Pro Ala His Val Pro Ala Pro Ser Pro Gln Gly
                725                 730                 735

Pro Gly Gly Leu Gln Gly Ala Ser Thr
            740                 745

<210>  17
<211>  659
<212>  PRT
<213>  Homo sapiens

<400>  17

Met Ala Ala Phe Ser Lys Tyr Leu Thr Ala Arg Asn Ser Ser Leu Ala
1               5                   10                  15

Gly Ala Ala Phe Leu Leu Leu Cys Leu Leu His Lys Arg Arg Arg Ala
                20                  25                  30

Leu Gly Leu His Gly Lys Lys Ser Gly Lys Pro Pro Leu Gln Asn Asn
            35                  40                  45

Glu Lys Glu Gly Lys Lys Glu Arg Ala Val Val Asp Lys Val Phe Phe
        50                  55                  60

Ser Arg Leu Ile Gln Ile Leu Lys Ile Met Val Pro Arg Thr Phe Cys
65                  70                  75                  80
```

```
Lys Glu Thr Gly Tyr Leu Val Leu Ile Ala Val Met Leu Val Ser Arg
                85                  90                  95

Thr Tyr Cys Asp Val Trp Met Ile Gln Asn Gly Thr Leu Ile Glu Ser
            100             105                 110

Gly Ile Ile Gly Arg Ser Arg Lys Asp Phe Lys Arg Tyr Leu Leu Asn
        115             120                 125

Phe Ile Ala Ala Met Pro Leu Ile Ser Leu Val Asn Asn Phe Leu Lys
    130             135                 140

Tyr Gly Leu Asn Glu Leu Lys Leu Cys Phe Arg Val Arg Leu Thr Lys
145                 150             155                     160

Tyr Leu Tyr Glu Glu Tyr Leu Gln Ala Phe Thr Tyr Tyr Lys Lys Gly
                165             170                 175

Asn Leu Asp Asn Arg Ile Ala Asn Pro Asp Gln Leu Leu Thr Gln Asp
            180             185                 190

Val Glu Lys Phe Cys Asn Ser Val Val Asp Leu Tyr Ser Asn Leu Ser
        195             200                 205

Lys Pro Phe Leu Asp Ile Val Leu Tyr Ile Phe Lys Leu Thr Ser Ala
        210             215                 220

Ile Gly Ala Gln Gly Pro Ala Ser Met Met Ala Tyr Leu Val Val Ser
225             230                 235                     240

Gly Leu Phe Leu Thr Arg Leu Arg Arg Pro Ile Gly Lys Met Thr Ile
                245             250                 255

Thr Glu Gln Lys Tyr Glu Gly Glu Tyr Arg Tyr Val Asn Ser Arg Leu
            260             265                 270
```

```
Ile Thr Asn Ser Glu Glu Ile Ala Phe Tyr Asn Gly Asn Lys Arg Glu
        275                 280                 285

Lys Gln Thr Val His Ser Val Phe Arg Lys Leu Val Glu His Leu His
        290                 295                 300

Asn Phe Ile Leu Phe Arg Phe Ser Met Gly Phe Ile Asp Ser Ile Ile
305                 310                 315                 320

Ala Lys Tyr Leu Ala Thr Val Val Gly Tyr Leu Val Val Ser Arg Pro
                325                 330                 335

Phe Leu Asp Leu Ser His Pro Arg His Leu Lys Ser Thr His Ser Glu
            340                 345                 350

Leu Leu Glu Asp Tyr Tyr Gln Ser Gly Arg Met Leu Leu Arg Met Ser
        355                 360                 365

Gln Ala Leu Gly Arg Ile Val Leu Ala Gly Arg Glu Met Thr Arg Leu
    370                 375                 380

Ala Gly Phe Thr Ala Arg Ile Thr Glu Leu Met Gln Val Leu Lys Asp
385                 390                 395                 400

Leu Asn His Gly Lys Tyr Glu Arg Thr Met Val Ser Gln Gln Glu Lys
                405                 410                 415

Gly Ile Glu Gly Val Gln Val Ile Pro Leu Ile Pro Gly Ala Gly Glu
            420                 425                 430

Ile Ile Ile Ala Asp Asn Ile Ile Lys Phe Asp His Val Pro Leu Ala
        435                 440                 445

Thr Pro Asn Gly Asp Val Leu Ile Arg Asp Leu Asn Phe Glu Val Arg
    450                 455                 460
```

```
Ser Gly Ala Asn Val Leu Ile Cys Gly Pro Asn Gly Cys Gly Lys Ser
465             470                 475                 480

Ser Leu Phe Arg Val Leu Gly Glu Leu Trp Pro Leu Phe Gly Gly Arg
            485                 490                 495

Leu Thr Lys Pro Glu Arg Arg Lys Leu Phe Tyr Val Pro Gln Arg Pro
            500                 505                 510

Tyr Met Thr Leu Gly Thr Leu Arg Asp Gln Val Ile Tyr Pro Asp Gly
        515                 520                 525

Arg Glu Asp Gln Lys Arg Lys Gly Ile Ser Asp Leu Val Gln Lys Glu
        530                 535                 540

Tyr Leu Asp Asn Val Gln Leu Gly His Ile Leu Glu Arg Glu Gly Gly
545                 550                 555                 560

Trp Asp Ser Val Gln Asp Trp Met Asp Val Leu Ser Gly Gly Glu Lys
                565                 570                 575

Gln Arg Met Ala Met Ala Arg Leu Phe Tyr His Lys Pro Gln Phe Ala
            580                 585                 590

Ile Leu Asp Glu Cys Thr Ser Ala Val Ser Val Asp Val Glu Gly Tyr
        595                 600                 605

Ile Tyr Ser His Cys Arg Lys Val Gly Ile Thr Leu Phe Thr Val Ser
        610                 615                 620

His Arg Lys Ser Leu Trp Lys His His Glu Tyr Tyr Leu His Met Asp
625                 630                 635                 640

Gly Arg Gly Asn Tyr Glu Phe Lys Gln Ile Thr Glu Asp Thr Val Glu
            645                 650                 655
```

Phe Gly Ser

<210> 18
<211> 763
<212> PRT
<213> Arabidopsis thaliana

<400> 18

Met Pro Ser Leu Gln Leu Leu Gln Leu Thr Glu Arg Gly Arg Gly Leu
1               5                   10                  15

Val Ala Ser Arg Arg Lys Ser Ile Leu Leu Ala Ala Gly Ile Val Ala
                20                  25                  30

Ala Gly Gly Thr Ala Val Tyr Leu Lys Ser Arg Val Ala Ser Arg Arg
                35                  40                  45

Pro Asp Ser Ser Arg Leu Cys Asn Gly Gln Ser Asp Asp Glu Thr
        50                  55                  60

Leu Glu Lys Leu Thr Ala Thr Asp Gln Asn Ala Lys Ile Thr Thr Lys
65                  70                  75                  80

Lys Lys Lys Gly Gly Gly Leu Lys Ser Leu Gln Val Leu Thr Ala Ile
                85                  90                  95

Leu Leu Ser Gln Met Gly Lys Met Gly Ala Arg Asp Leu Leu Ala Leu
                100                 105                 110

Val Ala Thr Val Val Phe Arg Thr Ala Leu Ser Asn Arg Leu Ala Lys
            115                 120                 125

Val Gln Gly Phe Leu Phe Arg Ala Ala Phe Leu Arg Arg Ala Pro Leu
        130                 135                 140

```
Phe Leu Arg Leu Ile Ser Glu Asn Ile Met Leu Cys Phe Met Leu Ser
145                 150                 155                 160

Thr Leu His Ser Thr Ser Lys Tyr Ile Thr Gly Ala Leu Ser Leu Arg
            165                 170                 175

Phe Arg Lys Ile Leu Thr Lys Ile Ile His Ser His Tyr Phe Glu Asn
            180                 185                 190

Met Val Tyr Tyr Lys Ile Ser His Val Asp Gly Arg Ile Thr His Pro
        195                 200                 205

Glu Gln Arg Ile Ala Ser Asp Val Pro Arg Phe Ser Ser Glu Leu Ser
    210                 215                 220

Asp Leu Ile Leu Asp Asp Leu Thr Ala Val Thr Asp Gly Ile Leu Tyr
225                 230                 235                 240

Ala Trp Arg Leu Cys Ser Tyr Ala Ser Pro Lys Tyr Ile Phe Trp Ile
                245                 250                 255

Leu Ala Tyr Val Leu Gly Ala Gly Thr Ala Ile Arg Asn Phe Ser Pro
                260                 265                 270

Ser Phe Gly Lys Leu Met Ser Lys Glu Gln Gln Leu Glu Gly Glu Tyr
            275                 280                 285

Arg Gln Leu His Ser Arg Leu Arg Thr His Ser Glu Ser Ile Ala Phe
    290                 295                 300

Tyr Gly Gly Glu Thr Arg Glu Glu Ser His Ile Gln Gln Lys Phe Lys
305                 310                 315                 320

Asn Leu Val Ser His Met Ser His Val Leu His Asp His Trp Trp Phe
                325                 330                 335
```

Gly Met Ile Gln Asp Phe Leu Leu Lys Tyr Leu Gly Ala Thr Val Ala
            340             345             350

Val Ile Leu Ile Ile Glu Pro Phe Phe Ser Gly His Leu Arg Pro Asp
            355             360             365

Asp Ser Thr Leu Gly Arg Ala Glu Met Leu Ser Asn Ile Arg Tyr His
            370             375             380

Thr Ser Val Ile Ile Ser Leu Phe Gln Ala Leu Gly Thr Leu Ser Ile
385             390             395             400

Ser Ser Arg Arg Leu Asn Arg Leu Ser Gly Tyr Ala Asp Arg Ile His
            405             410             415

Glu Leu Met Ala Val Ser Arg Glu Leu Ser Gly Asp Asp Lys Ser Ser
            420             425             430

Phe Gln Arg Asn Arg Ser Arg Asn Tyr Leu Ser Glu Ala Asn Tyr Val
            435             440             445

Glu Phe Ser Asp Val Lys Val Val Thr Pro Thr Gly Asn Val Leu Val
            450             455             460

Glu Asp Leu Thr Leu Arg Val Glu Gln Gly Ser Asn Leu Leu Ile Thr
465             470             475             480

Gly Pro Asn Gly Ser Gly Lys Ser Ser Leu Phe Arg Val Leu Gly Gly
            485             490             495

Gly Lys Met Gly Ala Arg Asp Leu Leu Ala Leu Val Ala Thr Val Val
            500             505             510

Phe Arg Thr Ala Leu Ser Asn Arg Leu Ala Lys Val Gln Gly Phe Leu
            515             520             525

```
Phe Arg Ala Ala Phe Leu Arg Arg Ala Pro Leu Phe Leu Arg Leu Ile
    530             535             540

Ser Glu Asn Ile Met Leu Cys Phe Met Leu Ser Gly Gln Glu Ser Glu
545             550             555                         560

Leu Leu Thr Glu Ile Gly Met Val Glu Leu Leu Lys Asn Val Asp Leu
                565             570             575

Glu Tyr Leu Leu Asp Arg Tyr Gln Pro Glu Lys Glu Val Asn Trp Gly
            580             585             590

Asp Glu Leu Ser Leu Gly Glu Gln Gln Arg Leu Gly Met Ala Arg Leu
            595             600             605

Phe Tyr His Lys Pro Lys Phe Ala Ile Leu Asp Glu Cys Thr Ser Ala
    610             615             620

Val Thr Thr Asp Met Glu Glu Arg Phe Ala Ala Lys Val Arg Ala Met
625             630             635             640

Gly Thr Ser Cys Ile Thr Ile Ser His Arg Pro Ala Leu Val Ala Phe
                645             650             655

His Asp Val Val Leu Ser Leu Asp Gly Glu Gly Gly Trp Ser Val His
            660             665             670

Tyr Lys Arg Asp Asp Ser Ala Leu Leu Thr Asp Ala Glu Ile Asp Ser
        675             680             685

Val Lys Ser Ser Asp Thr Asp Arg Gln Asn Asp Ala Met Val Val Gln
    690             695             700

Arg Ala Phe Ala Ala Ala Arg Lys Glu Ser Ala Thr Asn Ser Lys Ala
705             710             715             720
```

```
Gln Ser Tyr Gln Thr Gln Leu Ile Ala Arg Ser Pro Val Val Asp Lys
                725                 730                 735

Ser Val Val Leu Pro Arg Phe Pro Gln Pro Gln Thr Ser Gln Arg Ala
                740                 745                 750

Leu Pro Ser Arg Val Ala Ala Met Leu Asn Val
                755                 760

<210> 19
<211> 587
<212> PRT
<213> Arabidopsis thaliana

<400> 19

Leu Ile Pro Thr Ile Phe Asp Lys Gln Gly Ala Gln Leu Leu Ala Val
1               5                   10                  15

Ala Cys Leu Val Val Ser Arg Thr Leu Ile Ser Asp Arg Ile Ala Ser
                20                  25                  30

Leu Asn Gly Thr Thr Val Lys Tyr Val Leu Glu Gln Asp Lys Ala Ala
            35                  40                  45

Phe Val Arg Leu Ile Gly Leu Ser Val Leu Gln Ser Gly Ala Ser Ser
    50                  55                  60

Ile Ile Ala Pro Ser Leu Arg His Leu Thr Gln Arg Leu Ala Leu Gly
65                  70                  75                  80

Trp Arg Ile Arg Leu Thr Gln His Leu Leu Arg Asn Tyr Leu Arg Asn
                85                  90                  95

Asn Ala Phe Tyr Lys Val Phe His Met Ser Gly Asn Ser Ile Asp Ala
                100                 105                 110
```

```
Asp Gln Arg Leu Thr Arg Asp Leu Glu Lys Leu Thr Ala Asp Leu Ser
        115                 120                 125

Gly Leu Leu Thr Gly Met Val Lys Pro Ser Val Asp Ile Leu Trp Phe
    130                 135                 140

Thr Trp Arg Met Lys Leu Leu Thr Gly Gln Arg Gly Val Ala Ile Leu
145                 150                 155                 160

Tyr Thr Tyr Met Leu Leu Gly Leu Gly Phe Leu Arg Arg Val Ala Pro
                165                 170                 175

Asp Phe Gly Asp Leu Ala Gly Glu Glu Gln Gln Leu Glu Gly Lys Phe
            180                 185                 190

Arg Phe Met His Glu Arg Leu Asn Thr His Ala Glu Ser Ile Ala Phe
            195                 200                 205

Phe Gly Gly Gly Ala Arg Glu Lys Ala Met Val Asp Lys Lys Phe Arg
        210                 215                 220

Ala Leu Leu Asp His Ser Leu Met Leu Leu Arg Lys Lys Trp Leu Tyr
225                 230                 235                 240

Gly Ile Leu Asp Asp Phe Val Thr Lys Gln Leu Pro Asn Asn Val Thr
            245                 250                 255

Trp Gly Leu Ser Leu Leu Tyr Ala Leu Glu His Lys Gly Asp Arg Ala
            260                 265                 270

Leu Val Ser Thr Gln Gly Glu Leu Ala His Ala Leu Arg Tyr Leu Ala
        275                 280                 285

Ser Val Val Ser Gln Ser Phe Met Ala Phe Gly Asp Ile Leu Glu Leu
        290                 295                 300
```

```
His Lys Lys Phe Leu Glu Leu Ser Gly Gly Ile Asn Arg Ile Phe Glu
305                 310                 315                 320

Leu Asp Glu Phe Leu Asp Ala Ser Gln Ser Gly Val Thr Ser Glu Asn
                325                 330                 335

Gln Thr Ser Arg Leu Asp Ser Gln Asp Leu Leu Ser Phe Ser Glu Val
            340                 345                 350

Asp Ile Ile Thr Pro Ala Gln Lys Leu Met Ala Ser Lys Leu Ser Cys
        355                 360                 365

Glu Ile Val Ser Gly Lys Ser Leu Leu Val Thr Gly Pro Asn Gly Ser
    370                 375                 380

Gly Lys Thr Ser Val Phe Arg Val Leu Arg Asp Ile Trp Pro Thr Val
385                 390                 395                 400

Cys Gly Arg Leu Thr Lys Pro Ser Leu Asp Ile Lys Glu Leu Gly Ser
                405                 410                 415

Gly Asn Gly Met Phe Phe Val Pro Gln Arg Pro Tyr Thr Cys Leu Gly
            420                 425                 430

Thr Leu Arg Asp Gln Ile Ile Tyr Pro Leu Ser Lys Glu Glu Ala Glu
        435                 440                 445

Lys Arg Ala Ala Lys Leu Tyr Thr Ser Gly Glu Ser Ser Thr Glu Ala
    450                 455                 460

Gly Ser Ile Leu Asp Ser His Leu Lys Thr Ile Leu Glu Asn Val Arg
465                 470                 475                 480

Leu Val Tyr Leu Leu Glu Arg Asp Val Gly Gly Trp Asp Ala Thr Thr
                485                 490                 495
```

```
Asn Trp Glu Asp Ile Leu Ser Leu Gly Glu Gln Gln Arg Leu Gly Met
                500                 505                 510

Ala Arg Leu Phe Phe His Arg Pro Lys Phe Gly Val Leu Asp Glu Cys
            515                 520                 525

Thr Asn Ala Thr Ser Val Asp Val Glu Glu Gln Leu Tyr Arg Val Ala
        530                 535                 540

Arg Asp Met Gly Val Thr Phe Ile Thr Ser Ser Gln Arg Pro Ala Leu
545                 550                 555                 560

Ile Pro Phe His Ser Leu Glu Leu Arg Leu Ile Asp Gly Glu Gly Asn
                565                 570                 575

Trp Glu Leu Arg Ser Ile Glu Gln Thr Thr Glu
                580                 585

<210>  20
<211>  758
<212>  PRT
<213>  Saccharomyces cerevisiae

<400>  20

Met Gln Leu Asp Ser Gly Ala Arg Ile Met Tyr Ile Pro Glu Val Glu
1               5                   10                  15

Leu Val Asp Arg Gln Ser Pro Asp Asn Lys Phe Met Asn Ala Thr
                20                  25                  30

Asp Lys Lys Lys Arg Lys Arg Ile Phe Ile Pro Pro Lys Asp Asn Asp
            35                  40                  45

Val Tyr Glu His Asp Lys Phe Leu Phe Lys Asn Val Glu Leu Glu Arg
        50                  55                  60
```

```
Ala Lys Asn Ser Gln Leu Phe Tyr Ser Lys Phe Leu Asn Gln Met Asn
65                  70                  75                  80

Val Leu Ser Lys Ile Leu Ile Pro Thr Val Phe Asp Lys Asn Phe Leu
                85                  90                  95

Leu Leu Thr Ala Gln Ile Phe Phe Leu Val Met Arg Thr Trp Leu Ser
            100                 105                 110

Leu Phe Val Ala Lys Leu Asp Gly Gln Ile Val Lys Asn Ile Ile Ala
        115                 120                 125

Gly Arg Gly Arg Ser Phe Leu Trp Asp Leu Gly Cys Trp Phe Leu Ile
    130                 135                 140

Ala Val Pro Ala Ser Tyr Thr Asn Ser Ala Ile Lys Leu Leu Gln Arg
145                 150                 155                 160

Lys Leu Ser Leu Asn Phe Arg Val Asn Leu Thr Arg Tyr Ile His Asp
                165                 170                 175

Met Tyr Leu Asp Lys Arg Leu Thr Phe Tyr Lys Leu Ile Phe Asp Ala
            180                 185                 190

Lys Ala Ser Asn Ser Val Ile Lys Asn Ile Asp Asn Ser Ile Thr Asn
        195                 200                 205

Asp Val Ala Lys Phe Cys Asp Ala Thr Cys Ser Val Phe Ala Asn Ile
    210                 215                 220

Ala Lys Pro Val Ile Asp Leu Ile Phe Phe Ser Val Tyr Leu Arg Asp
225                 230                 235                 240

Asn Leu Gly Thr Val Gly Val Ala Gly Ile Phe Val Asn Tyr Phe Ile
                245                 250                 255
```

```
Thr Gly Phe Ile Leu Arg Lys Tyr Thr Pro Pro Leu Gly Lys Leu Ala
            260                 265                 270

Gly Glu Arg Ser Ala Ser Asp Gly Asp Tyr Tyr Asn Tyr His Leu Asn
        275                 280                 285

Met Ile Asn Asn Ser Glu Glu Ile Ala Phe Tyr Gln Gly Thr Ala Val
    290                 295                 300

Glu Arg Thr Lys Val Lys Glu Leu Tyr Asp Val Leu Met Glu Lys Met
305                 310                 315                 320

Leu Leu Val Asp Lys Val Lys Phe Gly Tyr Asn Met Leu Glu Asp Tyr
                325                 330                 335

Val Leu Lys Tyr Thr Trp Ser Gly Leu Gly Tyr Val Phe Ala Ser Ile
            340                 345                 350

Pro Ile Val Met Ser Thr Leu Ala Thr Gly Ile Asn Ser Glu Glu Lys
        355                 360                 365

Asn Met Lys Glu Phe Ile Val Asn Lys Arg Leu Met Leu Ser Leu Ala
    370                 375                 380

Asp Ala Gly Ser Arg Leu Met His Ser Ile Lys Asp Ile Ser Gln Leu
385                 390                 395                 400

Thr Gly Tyr Thr Asn Arg Ile Phe Thr Leu Leu Ser Val Leu His Arg
                405                 410                 415

Val His Ser Leu Asn Phe Asn Tyr Gly Ala Val Pro Ser Ile Leu Ser
            420                 425                 430

Ile Arg Thr Glu Asp Ala Ser Arg Asn Ser Asn Leu Leu Pro Thr Thr
        435                 440                 445
```

Asp Asn Ser Gln Asp Ala Ile Arg Gly Thr Ile Gln Arg Asn Phe Asn
            450                 455                 460

Gly Ile Arg Leu Glu Asn Ile Asp Val Ile Ile Pro Ser Val Arg Ala
465                 470                 475                 480

Ser Glu Gly Ile Lys Leu Ile Asn Lys Leu Thr Phe Gln Ile Pro Leu
                485                 490                 495

His Ile Asp Pro Ile Thr Ser Lys Ser Asn Ser Ile Gln Asp Leu Ser
            500                 505                 510

Lys Ala Asn Asp Ile Lys Leu Pro Phe Leu Gln Gly Ser Gly Ser Ser
            515                 520                 525

Leu Leu Ile Leu Gly Pro Asn Gly Cys Gly Lys Ser Ser Ile Gln Arg
        530                 535                 540

Ile Ile Ala Glu Ile Trp Pro Val Tyr Asn Lys Asn Gly Leu Leu Ser
545                 550                 555                 560

Ile Pro Ser Glu Asn Asn Ile Phe Phe Ile Pro Gln Lys Pro Tyr Phe
                565                 570                 575

Ser Arg Gly Gly Thr Leu Arg Asp Gln Ile Ile Tyr Pro Met Ser Ser
            580                 585                 590

Asp Glu Phe Phe Asp Arg Gly Phe Arg Asp Lys Glu Leu Val Gln Ile
            595                 600                 605

Leu Val Glu Val Lys Leu Asp Tyr Leu Leu Lys Arg Gly Val Gly Leu
            610                 615                 620

Thr Tyr Leu Asp Ala Ile Ala Asp Trp Lys Asp Leu Leu Ser Gly Gly
625                 630                 635                 640

```
Glu Lys Gln Arg Val Asn Phe Ala Arg Ile Met Phe His Lys Pro Leu
                645                 650                 655

Tyr Val Val Leu Asp Glu Ala Thr Asn Ala Ile Ser Val Asp Met Glu
                660                 665                 670

Asp Tyr Leu Phe Asn Leu Leu Lys Arg Tyr Arg Phe Asn Phe Ile Ser
                675                 680                 685

Ile Ser Gln Arg Pro Thr Leu Ile Lys Tyr His Glu Met Leu Leu Glu
        690                 695                 700

Ile Gly Glu Asn Arg Asp Gly Lys Trp Gln Leu Gln Ala Val Gly Thr
705                 710                 715                 720

Asp Glu Ala Ile Thr Ser Ile Asp Asn Glu Ile Glu Glu Leu Glu Arg
                725                 730                 735

Lys Leu Glu Arg Val Lys Gly Trp Glu Asp Glu Arg Thr Lys Leu Arg
                740                 745                 750

Glu Lys Leu Glu Ile Ile
        755

<210> 21
<211> 852
<212> PRT
<213> Saccharomyces cerevisiae

<400> 21

Met Ile Ser Thr Ala Ser Ala Phe Tyr Gln Lys His Arg Val Asn Leu
1               5                   10                  15

Leu Arg Ser Ser Tyr Ile Ile Leu Leu Leu Ala Thr Leu Tyr Asn Ser
                20                  25                  30
```

```
Asn Ser Ser Ser Ser Asn Asn Lys Thr Asp Lys Lys Asp Ser Glu Ser
        35                  40              45

Thr Val Leu Glu Asn Lys Lys Ile Glu Glu Gly Lys Glu Thr Ala Val
    50                  55              60

Asp Arg Glu Glu Asp Glu Ser Ser Lys Glu Glu Leu Thr Ile Val Ser
65                  70              75                      80

Lys His Ser Thr Asp Ser Glu Asp Gly Ala Ile Ile Ile Asp Lys Glu
            85                  90                  95

Ser Lys Thr Asn His Lys Gly Gly Glu Arg Lys Gly Lys Val Asp Phe
            100                 105                 110

Leu Phe Lys Leu Leu Leu His Asp Lys Lys Cys Leu Ile Leu Phe Ile
        115                 120                 125

Thr Gln Ala Ile Leu Leu Asn Ile Arg Thr Leu Leu Ser Leu Arg Val
        130                 135                 140

Ala Thr Leu Asp Gly Gln Leu Val Ser Thr Leu Val Arg Ala Gln Tyr
145                 150                 155                 160

Ala Asn Phe Thr Lys Ile Leu Leu Gly Lys Trp Met Ile Leu Gly Ile
            165                 170                 175

Pro Ala Ser Phe Ile Asn Ser Leu Ile Ser Tyr Thr Thr Lys Leu Cys
            180                 185                 190

Ala Val Thr Ile Asn Arg Lys Val Ser Asp Phe Leu Leu Ser Lys Tyr
        195                 200                 205

Leu Ser Asn His His Thr Phe Tyr Ser Val Ala Ser Ala Glu Ser Val
        210                 215                 220
```

```
Ser Glu Ile Gln Asp Asn Leu Thr Lys Asp Ile Tyr Thr Phe Ser Met
225                 230                 235                 240

Asn Ser Ser Leu Leu Leu Asn Gln Leu Leu Lys Pro Met Leu Asp Leu
            245                 250                 255

Ile Leu Cys Ser Phe Lys Leu Leu Thr Ser Asn Thr Ser Val Met Gly
            260                 265                 270

Glu Gly Thr Leu Ala Leu Gly Leu Ile Val Tyr Ala Ser Asn Ser Leu
            275                 280                 285

Leu Lys Leu Ile Gln Pro Asn Phe Thr Arg Leu Thr Met Ala Ser Ala
    290                 295                 300

Ser Leu Glu Ser Trp Phe Arg Ser Leu His Ser Asn Leu His Ser Ser
305                 310                 315                 320

Asn Glu Glu Ile Ala Leu Leu Arg Gly Gln Lys Arg Glu Leu Glu Asn
                325                 330                 335

Val Asp Tyr Ser Phe Tyr Arg Leu Val Leu Phe Leu Asn Arg Glu Ile
            340                 345                 350

Lys Ala Arg Ala Ile Tyr Asp Val Ala Thr Ala Phe Val Ile Lys Tyr
        355                 360                 365

Thr Trp Gly Ala Ala Gly Leu Val Leu Cys Ser Ile Pro Ile Phe Phe
    370                 375                 380

Lys Asn Lys Pro Ser Glu Asp Thr Leu Gln Leu Lys Glu Pro Gly Asn
385                 390                 395                 400

Asp Met Thr Ala Asp Phe Ile Thr Asn Arg Arg Leu Leu Val Thr Ala
            405                 410                 415
```

```
Ser Ser Ser Ile Gly Arg Phe Val Glu Leu Lys Arg Asn Ile Gln Gln
            420             425             430

Leu Arg Gly Ile Arg Leu Arg Leu Asn Lys Phe Asn Asp Leu Leu Asp
        435             440             445

Ala Asn Lys Gly Asp Asp Glu Lys Glu Pro Arg Asp Glu Arg Cys Ile
    450             455             460

Val Glu Tyr Asp Asp Ser Arg Ile Lys Phe Glu Asn Ile Pro Leu Ile
465             470             475                         480

Thr Pro Ala Asn Gln Val Leu Val Pro Glu Leu Ser Phe Asp Leu Lys
            485             490                     495

His Gly Asn His Leu Leu Ile Ile Gly Pro Asn Gly Cys Gly Lys Ser
            500             505             510

Ser Leu Phe Arg Ile Leu Gly Gly Leu Trp Pro Ile Arg Ala Thr Pro
        515             520             525

Asn Lys Asn His Gln Ser Lys Leu Ile Met Pro Arg Arg Thr Val Asp
    530             535             540

Arg Asp Cys Ala Ile Phe Tyr Leu Pro Gln Arg Pro Tyr Met Gly Asn
545             550             555                         560

Arg Ser Thr Phe Arg Glu Gln Ile Ile Tyr Pro Asp Ser Ile Glu Gln
            565             570             575

Phe Lys Glu Arg Tyr His Asn Asp Tyr Asp Leu Gly Asp Ala Asp Leu
            580             585             590

Ile Lys Ile Leu Gln Leu Leu Asp Leu Glu Asp Leu Val Thr Glu Asn
        595             600             605
```

```
Met Ser Leu Leu Ala Gln Arg Thr Ser Lys Asn Asp Ser Gln Gln
    610             615             620

Leu Ser Thr Glu Asp Asn Gln Ser Pro Cys Ala Ile Lys Val Arg Asp
625             630             635                     640

Ala Phe Ser Ile Val Arg Asn Trp Ser Glu Glu Leu Thr Ile Gly Val
                645             650                     655

Gln Gln Arg Leu Ala Met Ala Arg Met Tyr Tyr His Lys Pro Lys Phe
            660             665             670

Ala Val Leu Asp Glu Cys Thr Ser Ala Val Ala Pro Glu Met Glu Gln
            675             680             685

Arg Met Tyr Glu Asn Ala Gln Asn Phe Gly Ile Ser Leu Ile Ser Val
    690             695             700

Cys His Arg Thr Ser Leu Trp His Phe His Asn Tyr Leu Leu Lys Phe
705             710             715                     720

Asp Gly Lys Gly Gly Tyr Gln Phe Gly Pro Phe Asn Pro Lys Glu Arg
                725             730             735

Leu Cys Asn Glu Glu Lys Leu Leu Glu Leu Asn Ala Ile Leu Asp Gln
            740             745             750

Gln Val Pro Leu Trp Glu Arg Lys Leu Lys Asp Leu Thr Ile Ala Lys
            755             760             765

Glu Ser Asn Ile Ile Arg Lys Ser Glu Thr Asn Leu Asn Leu Phe Glu
    770             775             780

Lys Ile Glu Asp Pro Lys Thr Ser Lys Ser Asn Ala Leu Phe Asn Ala
785             790             795                     800
```

CERTIFICATE OF CORRECTION (continued)
U.S. Pat. No. 7,626,079 B2

```
Asn Lys Gly Gln Arg Ile Thr Ser Pro Thr Gly Gln Glu Thr Ser Lys
                805                 810                 815

Arg Leu Pro Leu Phe Ser Gln Pro Ser Ser Ser Ala Ser Ser Asn Leu
            820                 825                 830

Leu Arg Asn Asn Lys Ser Leu Asn Lys Lys Val Lys Thr Lys Lys Glu
        835                 840                 845

Glu Gly Lys Glu
    850
```

Signed and Sealed this

Ninth Day of March, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,626,079 B2 | Page 1 of 1 |
| APPLICATION NO. | : 10/486376 | |
| DATED | : December 1, 2009 | |
| INVENTOR(S) | : Baker et al. | |

It is certified that error appears in the above-identified patent and that said Letters Patent is hereby corrected as shown below:

On the Title Page

Item [*] Notice: Subject to any disclaimer, the term of this patent is extended or adjusted under 35 USC 154(b) by 111 days Delete the phrase "by 111 days" and insert -- by 201 days --

Signed and Sealed this

Thirty-first Day of August, 2010

David J. Kappos
*Director of the United States Patent and Trademark Office*